(12) United States Patent
Satish et al.

(10) Patent No.: US 12,268,477 B2
(45) Date of Patent: Apr. 8, 2025

(54) FLUID LOSS ESTIMATION OF MEDICAL ITEMS

(71) Applicant: Stryker Corporation, Portage, MI (US)

(72) Inventors: Siddarth Satish, Portola Valley, CA (US); Julian Thayn, Mountain View, CA (US)

(73) Assignee: Stryker Corporation, Portage, MI (US)

( * ) Notice: Subject to any disclaimer, the term of this patent is extended or adjusted under 35 U.S.C. 154(b) by 188 days.

(21) Appl. No.: 17/560,728

(22) Filed: Dec. 23, 2021

(65) Prior Publication Data
US 2022/0110532 A1 Apr. 14, 2022

Related U.S. Application Data

(63) Continuation of application No. 15/869,429, filed on Jan. 12, 2018, now Pat. No. 11,229,368.
(Continued)

(51) Int. Cl.
*A61B 5/02* (2006.01)
*A61B 5/00* (2006.01)
(Continued)

(52) U.S. Cl.
CPC ........ *A61B 5/02042* (2013.01); *A61B 5/7278* (2013.01); *A61B 5/743* (2013.01);
(Continued)

(58) Field of Classification Search
CPC .................................................. A61B 5/02042
See application file for complete search history.

(56) References Cited

U.S. PATENT DOCUMENTS 2,707,955 A 5/1955 Borden
3,182,252 A 5/1965 Den Berg
(Continued)

FOREIGN PATENT DOCUMENTS

CA 2870635 A1 10/2013
CN 101505813 A 8/2009
(Continued)

OTHER PUBLICATIONS

"Quantification of Blood Loss (QBL) Calculator." 2015. https://perinatology.com/calculators/Blood%20%20Loss%20Calculator.htm (Year: 2015).*
(Continued)

*Primary Examiner* — Meredith Weare
(74) *Attorney, Agent, or Firm* — Howard & Howard Attorneys PLLC

(57) ABSTRACT

A computer-implemented method and system for estimating fluid loss. A graphical representation of a container is displayed. User inputs to display elements may include incrementing or decrementing sliding markers to desired set positions. A first user input may indicate a volume of a second fluid, and a second user input may indicate a total volume of fluid. A first volume of a first fluid may be estimated based on the first and second user inputs. A graphical representation of the first volume of the first fluid may be displayed as a fluid level within the graphical representation of the container. A second volume of the first fluid contained in an absorbent article may be estimated based on a difference between a dry weight and a wet weight measured on a scale. A quantity of the first fluid may be estimated based on the first and second volumes.

16 Claims, 10 Drawing Sheets

Related U.S. Application Data

(60) Provisional application No. 62/446,333, filed on Jan. 13, 2017.

(51) Int. Cl.
| | |
|---|---|
| *A61B 10/00* | (2006.01) |
| *A61F 13/36* | (2006.01) |
| *G01G 19/414* | (2006.01) |
| A61F 13/84 | (2006.01) |
| A61M 1/00 | (2006.01) |
| G01G 23/365 | (2006.01) |

(52) U.S. Cl.
CPC .......... *A61B 5/7435* (2013.01); *A61B 5/7475* (2013.01); *A61B 10/0048* (2013.01); *A61F 13/36* (2013.01); *G01G 19/414* (2013.01); A61B 2505/05 (2013.01); A61F 2013/8491 (2013.01); A61M 1/60 (2021.05); A61M 2205/3393 (2013.01); G01G 23/365 (2013.01)

(56) References Cited

U.S. PATENT DOCUMENTS

| | | |
|---|---|---|
| 3,199,507 A | 8/1965 | Kamm |
| 3,367,431 A | 2/1968 | Baker |
| 3,646,938 A | 3/1972 | Haswell |
| 3,832,135 A | 8/1974 | Chlupsa et al. |
| 3,864,571 A | 2/1975 | Stillman et al. |
| 3,869,005 A | 3/1975 | Williams, Jr. |
| 3,948,390 A | 4/1976 | Ferreri |
| 4,105,019 A | 8/1978 | Haswell |
| 4,149,537 A | 4/1979 | Haswell |
| 4,190,153 A | 2/1980 | Olsen |
| 4,244,369 A | 1/1981 | McAvinn et al. |
| 4,295,537 A | 10/1981 | McAvinn et al. |
| 4,313,292 A | 2/1982 | McWilliams |
| 4,402,373 A | 9/1983 | Comeau |
| 4,422,548 A | 12/1983 | Cheesman et al. |
| 4,429,789 A | 2/1984 | Puckett |
| 4,512,428 A | 4/1985 | Bullivant |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,009,275 A | 4/1991 | Sheehan |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 7/1992 | Manion et al. |
| 5,190,059 A | 3/1993 | Fabian et al. |
| 5,227,765 A | 7/1993 | Ishizuka et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon |
| 5,369,713 A | 11/1994 | Schwartz et al. |
| 5,443,082 A | 8/1995 | Mewburn |
| 5,487,300 A * | 1/1996 | Brackett ................ B67D 7/08 73/201 |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,640,130 B1 | 10/2003 | Freeman et al. |
| 6,641,039 B2 | 11/2003 | Southard |
| 6,699,231 B1 | 3/2004 | Sterman |
| 6,728,561 B2 | 4/2004 | Smith et al. |
| 6,730,054 B2 | 5/2004 | Pierce et al. |
| 6,763,148 B1 | 7/2004 | Sternberg et al. |
| 6,777,623 B2 | 8/2004 | Ballard |
| 6,781,067 B2 | 8/2004 | Montagnino |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,255,003 B2 | 8/2007 | Schneiter |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | McCall |
| D611,731 S | 3/2010 | Levine |
| 7,670,289 B1 | 3/2010 | McCall |
| 7,703,674 B2 | 4/2010 | Stewart et al. |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,872,201 B1 | 1/2011 | Whitney |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,241,238 B2 | 8/2012 | Hiruma |
| 8,374,397 B2 | 2/2013 | Shpunt et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,639,226 B2 | 1/2014 | Hutchings et al. |
| 8,693,753 B2 | 4/2014 | Nakamura |
| 8,704,178 B1 | 4/2014 | Pollock et al. |
| 8,768,014 B2 | 7/2014 | Du et al. |
| 8,792,693 B2 | 7/2014 | Satish et al. |
| 8,823,776 B2 | 9/2014 | Tian et al. |
| 8,897,523 B2 | 11/2014 | Satish et al. |
| 8,983,167 B2 | 3/2015 | Satish et al. |
| 8,985,446 B2 | 3/2015 | Fleck et al. |
| 9,047,663 B2 | 6/2015 | Satish et al. |
| 9,171,368 B2 | 10/2015 | Satish et al. |
| 9,347,817 B2 | 5/2016 | Pollock et al. |
| 9,595,104 B2 | 3/2017 | Satish et al. |
| 9,652,655 B2 | 5/2017 | Satish et al. |
| 9,804,768 B1 | 10/2017 | Heilbrunn |
| 9,824,441 B2 | 11/2017 | Satish et al. |
| 9,936,906 B2 | 4/2018 | Satish et al. |
| 10,282,839 B2 | 5/2019 | Satish et al. |
| 10,555,675 B2 | 2/2020 | Satish et al. |
| 11,229,368 B2 * | 1/2022 | Satish .................... A61F 13/36 |
| 2003/0069509 A1 | 4/2003 | Matzinger et al. |

(56) References Cited

U.S. PATENT DOCUMENTS

| | | | |
|---|---|---|---|
| 2003/0095197 A1 | 5/2003 | Wheeler et al. | |
| 2003/0121704 A1 | 7/2003 | Breed | |
| 2003/0130596 A1 | 7/2003 | Goltz | |
| 2004/0031626 A1 | 2/2004 | Morris et al. | |
| 2004/0129678 A1 | 7/2004 | Crowley et al. | |
| 2005/0051466 A1 | 3/2005 | Carter et al. | |
| 2005/0163354 A1 | 7/2005 | Ziegler | |
| 2005/0265996 A1 | 12/2005 | Lentz | |
| 2006/0058593 A1 | 3/2006 | Drinan et al. | |
| 2006/0178578 A1 | 8/2006 | Tribble et al. | |
| 2006/0224086 A1 | 10/2006 | Harty | |
| 2007/0004959 A1 | 1/2007 | Carrier et al. | |
| 2007/0024946 A1 | 2/2007 | Panasyuk et al. | |
| 2007/0108129 A1 | 5/2007 | Mori | |
| 2007/0243137 A1 | 10/2007 | Hainfeld | |
| 2007/0287182 A1 | 12/2007 | Morris et al. | |
| 2008/0029416 A1 | 2/2008 | Paxton | |
| 2008/0030303 A1 | 2/2008 | Kobren et al. | |
| 2008/0045845 A1 | 2/2008 | Pfeiffer et al. | |
| 2008/0194906 A1 | 8/2008 | Mahony et al. | |
| 2009/0076470 A1 | 3/2009 | Ryan | |
| 2009/0080757 A1 | 3/2009 | Roger et al. | |
| 2009/0257632 A1 | 10/2009 | Lalpuria et al. | |
| 2009/0310123 A1 | 12/2009 | Thomson | |
| 2009/0317002 A1 | 12/2009 | Dein | |
| 2010/0003714 A1 | 1/2010 | Bachur, Jr. et al. | |
| 2010/0007727 A1 | 1/2010 | Torre-Bueno | |
| 2010/0025336 A1 | 2/2010 | Carter et al. | |
| 2010/0027868 A1 | 2/2010 | Kosaka et al. | |
| 2010/0066996 A1 | 3/2010 | Kosaka et al. | |
| 2010/0087770 A1 | 4/2010 | Bock | |
| 2010/0138053 A1* | 6/2010 | Kollep | A47J 31/4457 700/282 |
| 2010/0150759 A1 | 6/2010 | Mazur | |
| 2010/0262116 A1* | 10/2010 | Sowb | A61B 5/7445 604/500 |
| 2010/0280117 A1 | 11/2010 | Patrick et al. | |
| 2011/0066182 A1 | 3/2011 | Falus | |
| 2011/0118647 A1 | 5/2011 | Paolini | |
| 2011/0192745 A1 | 8/2011 | Min | |
| 2011/0196321 A1 | 8/2011 | Wudyka | |
| 2011/0200239 A1 | 8/2011 | Levine et al. | |
| 2011/0275957 A1 | 11/2011 | Bhandari | |
| 2011/0305376 A1 | 12/2011 | Neff | |
| 2011/0316973 A1 | 12/2011 | Miller et al. | |
| 2012/0000297 A1 | 1/2012 | Hashizume et al. | |
| 2012/0064132 A1 | 3/2012 | Aizawa | |
| 2012/0065482 A1 | 3/2012 | Robinson et al. | |
| 2012/0106811 A1 | 5/2012 | Chen et al. | |
| 2012/0127290 A1 | 5/2012 | Tojo et al. | |
| 2012/0210778 A1 | 8/2012 | Palmer et al. | |
| 2012/0257188 A1 | 10/2012 | Yan et al. | |
| 2012/0262704 A1 | 10/2012 | Zahniser et al. | |
| 2012/0309636 A1 | 12/2012 | Gibbons et al. | |
| 2012/0327365 A1 | 12/2012 | Makihira | |
| 2013/0011042 A1* | 1/2013 | Satish | G06T 5/00 382/134 |
| 2013/0034908 A1 | 2/2013 | Barstis et al. | |
| 2013/0088354 A1 | 4/2013 | Thomas | |
| 2013/0094996 A1 | 4/2013 | Janssenswillen | |
| 2013/0170729 A1 | 7/2013 | Wardlaw et al. | |
| 2013/0308852 A1 | 11/2013 | Hamsici et al. | |
| 2014/0079297 A1 | 3/2014 | Tadayon et al. | |
| 2014/0207091 A1 | 7/2014 | Heagle et al. | |
| 2014/0294237 A1 | 10/2014 | Litvak et al. | |
| 2014/0330094 A1 | 11/2014 | Pacione et al. | |
| 2015/0310634 A1 | 10/2015 | Babcock et al. | |
| 2016/0069743 A1 | 3/2016 | McQuilkin et al. | |
| 2016/0123998 A1 | 5/2016 | Macintyre et al. | |
| 2016/0189489 A1* | 6/2016 | Au | G07G 1/0072 235/383 |
| 2016/0331248 A1 | 11/2016 | Satish et al. | |
| 2016/0331282 A1 | 11/2016 | Satish et al. | |
| 2017/0011276 A1 | 1/2017 | Mehring et al. | |
| 2017/0023446 A1 | 1/2017 | Rietveld et al. | |
| 2017/0185739 A1* | 6/2017 | Gomez | G16H 10/60 |
| 2017/0186160 A1 | 6/2017 | Satish et al. | |
| 2017/0351894 A1 | 12/2017 | Satish et al. | |
| 2017/0352152 A1 | 12/2017 | Satish et al. | |
| 2018/0130279 A1* | 5/2018 | Ceccaroli | G07F 13/065 |
| 2018/0199827 A1 | 7/2018 | Satish et al. | |
| 2019/0008427 A1 | 1/2019 | Satish et al. | |

FOREIGN PATENT DOCUMENTS

| | | | |
|---|---|---|---|
| JP | S59161801 U | 10/1984 | |
| JP | S61176357 A | 8/1986 | |
| JP | S62144652 U | 9/1987 | |
| JP | H06510210 A | 11/1994 | |
| JP | H07308312 A | 11/1995 | |
| JP | H1137845 A | 2/1999 | |
| JP | 2000227390 A | 8/2000 | |
| JP | 2002331031 A | 11/2002 | |
| JP | 2003075436 A | 3/2003 | |
| JP | 2005052288 A | 3/2005 | |
| JP | 3701031 B2 | 9/2005 | |
| JP | 2006280445 A | 10/2006 | |
| JP | 2007101482 A | 4/2007 | |
| JP | 2008055142 A | 3/2008 | |
| JP | 2008519604 A | 6/2008 | |
| JP | 2010516429 A | 5/2010 | |
| JP | 2011036371 A | 2/2011 | |
| JP | 2011515681 A | 5/2011 | |
| JP | 2011252804 A | 12/2011 | |
| WO | 9217787 A1 | 10/1992 | |
| WO | 9639927 A1 | 12/1996 | |
| WO | 2006053208 A1 | 5/2006 | |
| WO | 2008094703 A2 | 8/2008 | |
| WO | 2009117652 A1 | 9/2009 | |
| WO | 2011019576 A1 | 2/2011 | |
| WO | 2011145351 A1 | 11/2011 | |
| WO | 2013009709 A2 | 1/2013 | |
| WO | 2013172874 A1 | 11/2013 | |
| WO | 2013173356 A1 | 11/2013 | |
| WO | 2015160997 A1 | 10/2015 | |
| WO | WO-2016174635 A1 * | 11/2016 | G06F 3/0488 |

OTHER PUBLICATIONS

"Cumulative Quantitative Assessment of Blood Loss." CMQCC Obstetric Hemorrhage Toolkit. Mar. 24, 2015. (Year: 2015).*

"Quantification of Blood Loss (QBL) Calculator." 2015 https://www.perinatotogy.com/calculators/Blood%20%20Loss%20Calculator.htm (Year: 2015).

ACOG (2012). "Optimizing protocols in obstetrics," Series 2, 25 total pages.

Adkins, A.R. et al. (2014). "Accuracy of blood loss estimations among anesthesia providers," AANA Journal 82(4):300-306.

Aklilu, A. Gauss Surgical Measures Blood Loss with a Smartphone. Jun. 14, 2012. <http://www.health2con.com/news/2012/06/14/gauss-surgical-measur- es-blood-loss-with-a-smartphone/>, 6 pages.

Al-Kadri, H.M. et al. (2014). "Effect of education and clinical assessment on the accuracy of post partum blood loss estimation," BMC Preg. Childbirth 14:110, 7 total pages.

Awhonn Practice Brief (2014). "Quantification of blood loss: AWHONN practice brief No. 1," AWHONN p. 1-3.

Bellad, et al. (2009). "Standardized Visual Estimation of Blood Loss during Vaginal Delivery with Its Correlation Hematocrit Changes—A Descriptive Study." South Asian Federation of Obstetrics and Gynecology 1:29-34.

Bose, P. et al. (2006). "Improving the accuracy of estimated blood loss at obstetric haemorrhage using clinical reconstructions," BJOG 113(8):919-924.

Corrected Notice of Allowability dated Sep. 15, 2017, for U.S. Appl. No. 14/687,842, filed Apr. 15, 2015, 2 pages.

Eipe, N. et al. (2006). "Perioperative blood loss assessment—How accurate?" Indian J. Anaesth. 50(1):35-38.

Extended European Search Report dated Apr. 1, 2015, for EP Application No. 12 810 640.8, filed on Jul. 9, 2012, 8 pages.

(56) References Cited

OTHER PUBLICATIONS

Extended European Search Report dated Jul. 12, 2019, for EP Application No. 19 156 549.8, filed on Jul. 9, 2012, 8 pages.
Extended European Search Report dated Jul. 26, 2017, for EP Application No. 15 780 653.0, filed on Apr. 15, 2015, 12 pages.
Extended European Search Report dated Jul. 9, 2019, for EP Application No. 16 880 150.4, filed on Dec. 23, 2016, 9 pages.
Extended European Search Report dated Nov. 17, 2015, for EP Application No. 13 790 449.6, filed on Jan. 10, 2013, 8 pages.
Extended European Search Report dated Nov. 23, 2015, for EP Application No. 13 790 688.9, filed on May 14, 2013, 9 pages.
Extended European Search Report dated Nov. 4, 2016, for EP Application No. 16 183 350.4, filed on Jul. 9, 2012, 9 pages.
Final Office Action dated Aug. 26, 2016, for U.S. Appl. No. 13/894,054, filed May 14, 2013, 7 pages.
Final Office Action dated Feb. 12, 2016, for U.S. Appl. No. 13/544,664, filed Jul. 9, 2012, 9 pages.
Final Office Action dated Jul. 26, 2016, for U.S. Appl. No. 14/876,628, filed Oct. 6, 2015, 5 pages.
Habak, P.J. et al. (2016). "A comparison of visual estimate versus calculated estimate of blood loss at vaginal delivery," British J. Med. Medical Res. 11 (4):1-7.
Holmes, A.A. et al. (2014). "Clinical evaluation of a novel system for monitoring surgical hemoglobin loss," Anesth. Analg. 119(3):588-594.
International Search Report dated Jul. 24, 2015, for PCT Application No. PCT/US2015/026036, filed on Apr. 15, 2015, 2 pages.
International Search Report dated Mar. 26, 2013, for PCT Application No. PCT/US2013/021075, filed on Jan. 10, 2013, 2 pages.
International Search Report dated Mar. 30, 2017, for PCT Application No. PCT/US2016/068540, filed on Dec. 23, 2016, 3 pages.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.
Jones, R. (2015). "Quantitative measurement of blood loss during delivery," AWHONN p. S41.
Kamiyoshihara, M. et al. (2008). "The Utility of an Autologous Blood Salvage System in Emergency Thoracotomy for a Hemothorax After Chest Trauma," Gen. Thorac. Cardiovasc. Surg. 56:222.
Lyndon, A. et al. (2010). "Blood loss: Clinical techniques for ongoing quantitative measurement," CMQCC Obstetric Hemorrhage Toolkit, pp. 1-7.
Lyndon, A. et al. (2015). "Cumulative quantitative assessment of blood loss," CMQCC Obstetric Hemorrhage Toolkit Version 2.0, pp. 80-85.
Manikandan, D. et al. (2015). "Measurement of blood loss during adenotonsillectomy in children and factors affecting it," Case Reports in Clinical Medicine 4:151-156.
Merck for Mother's Program (2012). Blood loss measurement: Technology opportunity assessment, 9 total pages.
Non-Final Of523fice Action dated Aug. 13, 2015, for U.S. Appl. No. 13/544,664, filed Jul. 9, 2012, 8 pages.
Non-Final Office Action dated Apr. 11, 2018, for U.S. Appl. No. 15/416,986, filed Jan. 26, 2017, 6 pages.
Non-Final Office Action dated Apr. 20, 2017, for U.S. Appl. No. 13/894,054, filed May 14, 2013, 7 pages.
Non-Final Office Action dated Aug. 2, 2016, for U.S. Appl. No. 13/544,664, filed Jul. 9, 2012, 6 pages.
Non-Final Office Action dated Dec. 15, 2015, for U.S. Appl. No. 14/876,628, filed Oct. 6, 2015, 8 pages.
Non-Final Office Action dated Feb. 21, 2019, for U.S. Appl. No. 15/594,017, filed May 12, 2017, 23 pages.
Non-Final Office Action dated Mar. 20, 2015, for U.S. Appl. No. 14/613,807, filed Feb. 4, 2015, 8 pages.
Non-Final Office Action dated Mar. 24, 2017, for U.S. Appl. No. 14/687,842, filed Apr. 15, 2015, 27 pages.
Non-Final Office Action dated Mar. 30, 2016, for U.S. Appl. No. 13/894,054, filed May 14, 2013, 9 pages.
Non-Final Office Action dated May 9, 2014, for U.S. Appl. No. 13/544,679, filed Jul. 9, 2012, 7 pages.—(1.31).
Non-Final Office Action dated Oct. 19, 2018, for U.S. Appl. No. 15/390,017, filed Dec. 23, 2016, 12 pages.
Non-Final Office Action dated Sep. 5, 2014, for U.S. Appl. No. 13/738,919, filed Jan. 10, 2013, 8 pages.
Notice of Allowance dated Aug. 3, 2017, for U.S. Appl. No. 14/687,842, filed Apr. 15, 2015, 9 pages.
Notice of Allowance dated Feb. 15, 2017, for U.S. Appl. No. 13/544,664, filed Jul. 9, 2012, 10 pages.
Notice of Allowance dated Jan. 24, 2019, for U.S. Appl. No. 15/416,986, filed Jan. 26, 2017, 9 pages.
Notice of Allowance dated Jun. 25, 2015, for U.S. Appl. No. 14/613,807, filed Feb. 4, 2015, 10 pages.
Notice of Allowance dated May 12, 2014, for U.S. Appl. No. 13/544,646, filed Jul. 9, 2012, 10 pages.
Notice of Allowance dated May 3, 2019, for U.S. Appl. No. 15/390,017, filed Dec. 23, 2016, 11 pages.
Notice of Allowance dated Nov. 10, 2014, for U.S. Appl. No. 13/738,919, filed Jan. 10, 2013, 10 pages.
Notice of Allowance dated Nov. 20, 2017, for U.S. Appl. No. 13/894,054, filed May 14, 2013, 8 pages.
Notice of Allowance dated Oct. 26, 2016, for U.S. Appl. No. 14/876,628, filed Oct. 6, 2015, 11 pages.
Notice of Allowance dated Sep. 3, 2014, for U.S. Appl. No. 13/544,679, filed Jul. 9, 2012, 8 pages.
Pogorelc, D. iPads in the OR: New Mobile Platform to Monitor Blood Loss During Surgery. MedCityNews, Jun. 6, 2012 http://medcitynews.com/2012/06/ipads-in-the-or-new-mobile-platform-to-mon- itor-blood-loss-during-surgery, 4 pages.
Roston, A.B. et al. (2012). "Chapter 9: Blood loss: Accuracy of visual estimation," in A comprehensive textbook of postpartum hemorrhage: An essential clinical reference for effective management, 2.sup.nd edition, Sapiens publishing, pp. 71-72.
Sant, et al. "Exsanguinated Blood Volume Estimation Using Fractal Analysis of Digital Images." Journal of Forensic Sciences 57.3 (2012): 610-17.
Schorn, M.N. (2010). "Measurement of blood loss: Review of the literature," J. Midwifery and Women's Health 55 (1):20-27.
Sukprasert, M. et al. (2006). "Increase accuracy of visual estimation of blood loss from education programme," J. Med. Assoc. Thai 89(suppl. 4):S54-S59.
U.S. Appl. No. 15/943,561, filed Apr. 2, 2018, by Satish et al.
Written Opinion of the International Searching Authority dated Jul. 24, 2015, for PCT Application No. PCT/U523S2015/026036, filed on Apr. 15, 2015, 6 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Mar. 30, 2017, for PCT Application No. PCT/US2016/068540, filed on Dec. 23, 2016, 8 pages.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.

* cited by examiner enter quantity of each substrate    weight: 178 g

| + gauze 0 − | + vag packs 0 − |
|---|---|
| + count bag 0 − | + pads 0 − |
| + chux 0 − | + laps 3 − |

[ analyze ]

scale status: connected

FIG. 3

FLUID LOSS ESTIMATION OF MEDICAL ITEMS

CROSS-REFERENCE TO RELATED APPLICATIONS

This is a continuation of copending U.S. application Ser. No. 15/869,429, filed Jan. 12, 2018, which claims priority to and all the benefits of U.S. Provisional Application No. 62/446,333, filed on Jan. 13, 2017, each of which is hereby incorporated by reference in its entirety.

TECHNICAL FIELD

This invention relates generally to the field of tracking fluid loss, and more specifically to new and useful systems and methods for estimating blood loss during a medical procedure.

BACKGROUND

Inaccurate estimation of fluid loss (e.g., blood) from a patient, such as during a medical procedure, may put the patient's health at risk. For example, accurate measurement of blood lost by a mother after childbirth may help quickly diagnose a life-threatening instance of postpartum hemorrhage, which is a leading cause of maternal mortality. Underestimation of patient blood loss may lead to delayed resuscitation and transfusion, increased risk of infections, tissue death, or even patient death, such as in the event of hemorrhage. Furthermore, overestimation of patient blood loss may result in the unnecessary consumption of transfusion-grade blood, and may lead to shortages of transfusion-grade blood that is needed for other patients.

Furthermore, inaccurate estimation may be a significant contributor to high operating and medical costs for hospitals, clinics, and other medical facilities. For example, unnecessary blood transfusions, resulting from overestimation of patient blood loss, may lead to higher operating costs for medical institutions. Additionally, delayed blood transfusions, resulting from underestimation of patient blood loss, have been associated with billions of dollars in avoidable patient infections and re-hospitalizations annually. Thus, it is desirable to have more accurate systems and methods for characterizing fluids from a patient.

SUMMARY

Generally, in one variation of a computer-implemented method for quantifying fluid loss from a patient, the method includes estimating a first volume of a first fluid (e.g., blood) contained in at least one item, displaying a graphical representation of a container with user inputs on a display, estimating the second volume of the first fluid in the container based at least in part on at least one of the user inputs, and estimating a quantity (e.g., volume, volumetric rate of loss) of the first fluid based at least in part on the estimated first and second volumes of the first fluid. The at least one item containing the first volume of the first fluid may include, for example, a surgical textile or a canister. The first volume of fluid may be estimated based on a difference between a dry weight of the item and a measured wet weight of the item when the item contains the first volume of the first fluid. Additionally, in some variations, the first volume of fluid may be estimated by dividing the difference between dry and wet weights of the item by a density of the first fluid. Furthermore, the graphical representation may include a first display element for receiving a first user input indicating the volume of the second fluid in the container, and a second display element for receiving a second user input indicating a total fluid volume in the container, where the second volume of the first fluid in the container may be based on at least one of the first and second user inputs. Additional volumes of the first fluid (e.g., collected in at least a second item, further collected to the same container or another container) may be estimated in similar manners. For example, the method may, in some variations, include estimating a quantity of the first fluid further based at least in part on an estimated third volume of the first fluid in a second container (e.g., a canister) as detected based on image processing techniques, weighing of the second container, user input received by a third display element, etc. In some variations, the method may include updating the estimated quantity of the first fluid to include the additional estimated volumes of the first fluid. Furthermore, an alert or alarm to the user may be provided, for example, if the total estimated quantity of the first fluid meets a predetermined threshold (e.g., indicating excessive or dangerous volume of blood lost or volumetric rate of blood lost).

In some variations, the method may include identifying a weighing event corresponding to the item being placed on a scale and receiving the wet weight in response to identifying the weighing event. A weighing event may be identified, for example, based on detection of a weight measurement meeting a predetermined threshold value and/or detecting a stable weight measurement for at least a predetermined period of time.

The method may include displaying a graphical user interface, including the graphical representation of the container and its display elements. For example, the graphical user interface may include a display prompting the user to input a quantity and/or type of item being weighed. The method may include receiving such user input and receiving a dry weight associated with the item type. In one exemplary variation, the method may include displaying a graphical representation of a container that is generally triangular (e.g., representing a V-shaped blood collection drape). In this exemplary variation, the graphical representation may include one display element corresponding to a volume of amniotic fluid, and another display element corresponding to a volume of blood. The display elements may be user-manipulable sliding markers, or other suitable elements for receiving user input of one or more fluid volumes.

In some variations, the method may further include receiving an aggregate weight of one or more weighed items of an item type and estimating a number of weighed items based at least in part on the aggregate weight and a dry weight associated with the item type. This may, for example, help facilitate counting and tracking of items (e.g., surgical sponges or other substrates described herein) used during the medical procedure, such as for reducing risk of inadvertent foreign object retention in the patient.

Generally, in one variation of a system for quantifying fluid from a patient, the system includes a wireless scale configured to measure a wet weight of at least one item containing a first volume of a first fluid, a display configured to display a graphical representation of a container containing a volume of a second fluid and a second volume of the first fluid, and a processor coupled to the wireless scale and the display. The graphical representation may include a first display element for receiving a first user input indicating the volume of the second fluid in the container and a second display element for receiving a second user input indicating a total fluid volume in the container. The processor may be configured to estimate the first volume of the first fluid in the item based on a difference between a dry weight of the item and a set weight of the item, estimate the second volume of the first fluid in the container based on at least one of the first and second user inputs, and estimate a quantity of the first fluid based at least in part on the estimated first and second volumes of the first fluid. The system may further include an optical sensor. In some variations of the system, the processor may be configured to perform one or more various aspects of the methods described above.

BRIEF DESCRIPTION OF THE DRAWINGS

FIG. 3 is an exemplary user interface prompting a user input of a quantity of one or more items, such as for weighing.

DETAILED DESCRIPTION

Figure 1:
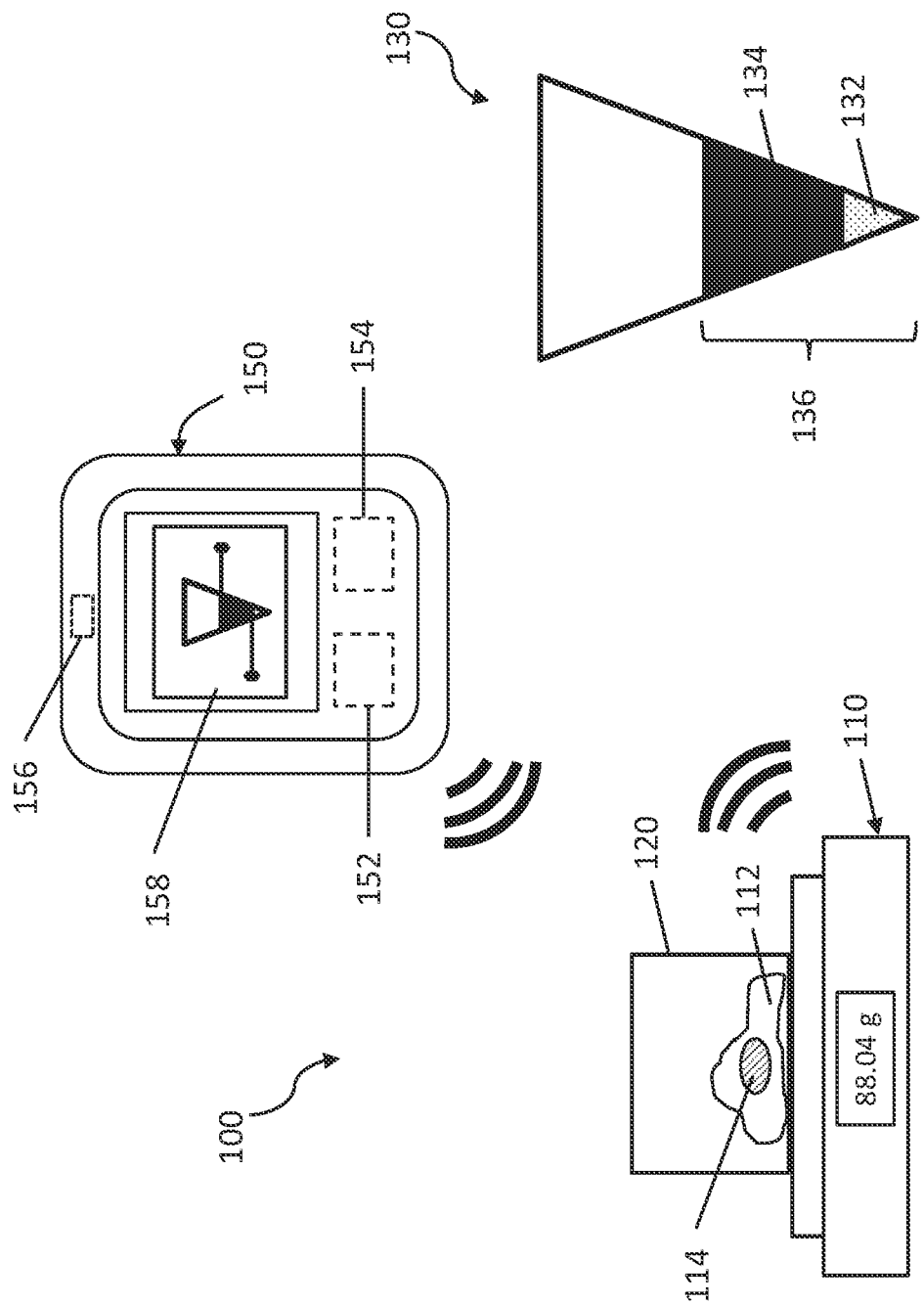
FIG. 1 is an illustrative schematic of one variation of a system for quantifying fluid from a patient.

Examples of various aspects and variations of the invention are described herein and illustrated in the accompanying drawings. The following description is not intended to limit the invention to these embodiments, but rather to enable a person skilled in the art to make and use this invention.
Overview Generally, the methods and systems described herein may be used to quantify fluids that are lost by a patient during a medical procedure (e.g., labor and delivery, surgical procedure, etc.). For example, the methods and systems may be used to track or otherwise estimate a quantity of fluid (e.g., blood) lost by a patient throughout a medical procedure, and the estimates may be updated and displayed in substantially real-time during the procedure and/or at the conclusion of the procedure. In some variations, estimated quantities of a fluid of interest from multiple sources may be aggregated to generate an estimate of total loss of the fluid. Additionally or alternatively, at least some fluid-collecting items (e.g., surgical textiles) may be tracked and accounted for via weighing and/or counting, such as for reducing the risk of inadvertently retaining foreign objects in the patient.

For example, during a medical procedure, extracorporeal fluids (e.g., blood) that are lost by the patient may be collected with surgical textiles or other absorbent items, such as surgical sponges (e.g., laparotomy sponges), surgical dressings, surgical gauze, surgical towels, absorbent pads or drapes (e.g., chux pads), vaginal packs and/or other textiles or absorbent items, etc. Textiles or absorbent items may be placed in a bag (e.g., sponge count bag) for tracking purposes, hygienic purposes, etc. Additionally or alternatively, extracorporeal fluids that are lost by the patient may be collected in a container, such as a canister. Some applications of the methods and systems may involve collection of lost fluids with a specialized container. For example, during labor and delivery procedures, a drape with at least one pocket (e.g., a blood collection drape with a triangular pocket) may be placed under the patient for collecting blood, amniotic fluid, urine, etc. The quantity of fluid collected in at least some types of items, such as surgical textiles and/or canisters, may be estimated based on a measured weight (mass) of the item when containing fluid. In some variations, multiple batches of such items may be weighed (e.g., as each batch of one or more textiles become saturated) and aggregated into a running total or overall estimate of the quantity of fluid lost by the patient during the procedure. Such estimates may, in some variations, be combined with estimates of fluid collected in batches and/or cumulatively over time in some other types of items, such as canisters or blood collection drapes. For example, total volume of fluid and/or total rate of fluid loss may be estimated at any particular point during the procedure and/or post-procedure.

The methods and systems described herein may be used in a variety of settings, including in a hospital or clinic setting (e.g., operating or clinic setting), a military setting (e.g., battlefield) or other suitable medical treatment settings. This information can be used to improve medical treatment of patients, as well as reduce costs to medical institutions and patients. For example, medical practitioners (e.g., nurses, surgeons) who receive this information during and/or after a medical procedure may be able to make more appropriate decisions for treatment of the patient (such as determining whether to provide a blood transfusion to the patient and how much blood is necessary) based on more accurate information on patient status. With more accurate information on the patient's fluid loss, practitioners may be able to, for example, avoid providing unnecessary blood transfusions (which deplete inventory and increase risk of complications due to transfusions), while also avoiding delayed blood transfusions (which risk patient health).

Figure 2:
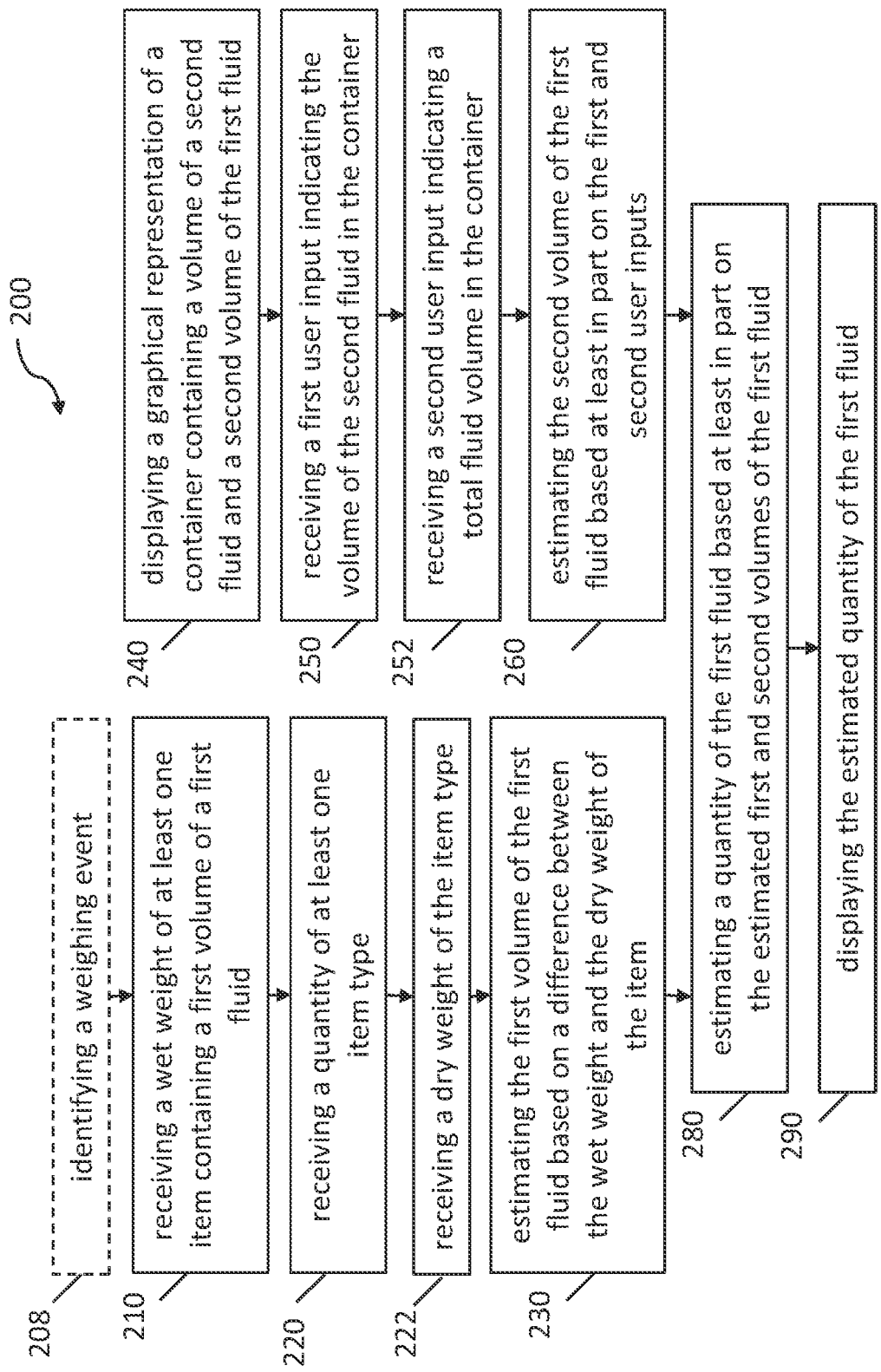
FIG. 2 is an illustrative flowchart schematic of one variation of a method for quantifying fluid from a patient.

The methods described herein may be computer-implemented and performed at least in part by one or more processors. For example, as shown in FIG. 1, in one variation, the method may be performed at least in part by a computer device such as a mobile device 150 (e.g., tablet, smartphone, etc.) in a delivery room, an operating room, or other medical site. However, some or all of the method may be performed by one or more processors that are separate from the mobile device 150 (e.g., on-site in the room or remotely outside the room). Other aspects of variations of methods and systems for quantifying fluids from a patient are described in further detail herein.
Methods for Quantifying Fluids As shown in FIG. 2, in some variations, a computer-implemented method 200 for quantifying fluids from a patient may include estimating the first volume of a first fluid based on a difference between a wet weight and a dry weight of the item 230. The method may further include receiving a wet weight of at least one item 210 containing a first volume of a first fluid, receiving a quantity of at least one item type 220, receiving a dry weight of the item type 222, such that the received wet weight and dry weight may be used to estimate the first volume of the first fluid. The method 200 may further include displaying a graphical representation of a container 240 containing a volume of a second fluid and a second volume of the first fluid, receiving a first user input 250 indicating the volume of the second fluid in the container, receiving a second user input 252 indicating a total fluid volume in the container, and estimating the second volume of the first fluid 260 based on at least one of the first and second user inputs. Furthermore, the method 200 may include estimating a quantity of the first fluid 280 based at least in part on the estimated first and second volumes of the first fluid, and may include displaying the estimated quantity of the first fluid 290. Estimates of fluid collected via other sources (estimates generated by weighing and/or received through user input) may additionally or alternatively be used to quantify fluid from the patient, as further described herein.

For example, in one exemplary variation, the method may be used to quantify blood from a patient undergoing a labor and delivery procedure. Some of the blood lost by the patient may be collected with one or more types of surgical textiles or other substrates, and the quantity of blood in these substrates may be estimated based on weight of the substrates. Additionally or alternatively, some of the blood lost by the patient may be collected and estimated with a blood collection drape (e.g., collecting from underneath the patient) and/or a canister (e.g., collected via suction wand, etc.). Estimates of blood from the weighed items and the other fluid-collecting items may be displayed separately (e.g., according to each fluid-collecting item) and/or may be summed and displayed as an aggregate estimate of blood lost by the patient.

Weighed Fluid-Collecting Items

As described above, some items or other substrates may be used to soak or collect fluids lost by a patient. The amount of fluid collected in each item may generally be estimated using a difference between the wet weight of the item (the weight of the item including the fluid to be estimated) and a dry weight of the item (the weight of the item without any fluid). Accordingly, in some variations, the method may include receiving a wet weight of at least one item 210 and receiving a dry weight of the item (as further described below).

For example, as shown in FIG. 1, the wet weight of the item may be measured with a scale 110 and communicated to a processor such as a processor 154 in a mobile device 150. Before the scale measures the wet weight of the item, the scale may first be tared or zeroed in order to set a baseline reference value relative to which the wet weight is determined. In some variations, the scale may be tared while no fluid-collecting items are placed on the scale, such that the baseline reference value may incorporate substantially no pre-existing weight placed on the scale or may incorporate a substantially empty receptacle (e.g., bucket 120) configured to receive fluid-collecting items. For example, each batch or multiple batches of fluid-collecting items may be separately weighed and analyzed, then removed prior to the placement of a subsequent batch on the scale. Alternatively, the scale may be tared while one or more previously-analyzed batches of items are placed on the scale, such that only the weight of an additional, subsequent batch of items is used and analyzed for fluid content in the additional batch.

In some variations, taring may be triggered by a user with a user interface that is configured to remotely communicate a tare action to the scale. Such remote taring may be triggered, for example, by tactilely interacting with a displayed user interface (e.g., on a touchscreen on a mobile device 150 or other device), by voice command, foot pedal, or any other suitable user interface. Additionally or alternatively, taring may be triggered by the user pressing a button or other element located on the scale itself. In yet other variations, the method may include automatically taring the scale based on one or more conditions. In one variation, the method may include detecting a predetermined type or sequence of events and taring the scale in response to detecting the predetermined type or sequence of events. For example, in response to detecting that a batch of fluid-collecting items has been placed on the scale or weighed and analyzed (as indicated, for example, by user input via a user interface), and subsequently removed (as indicated, for example, by a sudden decrement in measured weight on the scale), the method may include automatically taring the scale to prepare the weighing and analysis of the next batch of fluid-collecting items. In another variation, taring may automatically occur after a predetermined length of time (e.g., ten seconds, thirty seconds, one minute, five minutes, etc.) without any significant change in detected weight on the scale. In yet another variation, taring may automatically occur whenever a negative weight is measured. For example, taring may automatically occur if a negative weight is measured for a period of time equal to or exceeding a predetermined amount of time, such as at least about 0.5 seconds, at least about 1 second, at least about 2 seconds, at least about 5 seconds, etc.

Following taring of the scale, as shown in FIG. 1, the user may place a batch including at least one item 112 containing fluid 114 (e.g., a surgical textile at least partially saturated with blood) in a receptacle 120 on a scale 110 (or alternatively, directly on the scale 110), which measures the wet weight of the item 112. Generally, the scale 110 may communicate the measured wet weight (wirelessly and/or via a wired connection) to a processor that receives the wet weight value for analysis as described elsewhere herein.

In some variations, as shown in FIG. 2A, the method may include identifying a weighing event 208 and receiving the wet weight of the item 210 in response to detecting the weighing event. Generally, a weighing event may correspond to placement of at least one fluid-collecting item on the scale. For example, a weighing event may be determined based on detection of an increase in measured weight beyond a predetermined weight threshold. For example, the predetermined weight threshold may be a value ranging between about 5 grams and about 15 grams, between about 7 grams and about 13 grams, or about 10 grams, etc.). In some variations, the predetermined weight threshold may differ depending on the type of item being measured (e.g., which may be known based on user input, as described below, and entered by the user before the user places the batch of items for weighing on the scale). For example, the predetermined weight threshold may be similar in value to a dry weight of a user-selected item type, or expected combined dry weight of multiple items of one or more user-selected item types.

In some variations, the predetermined weight threshold may be determined based at least in part on one or more previously measured dry weights of one or more items, where the measured dry weights are stored in memory as further described below. For example, the predetermined weight threshold may be based at least in part on the lowest of one or more previously measured and stored dry weights of an item. In one illustrative example, the predetermined weight threshold may be equal to the lowest of all previously measured and stored dry weights (e.g., of all weighed items, of all weighed items of the same type as the item currently being measured, etc.) or a fraction of such lowest dry item weight (e.g., the lowest previously measured and recorded dry weight multiplied by a scaling factor such as a factor between about 0.1 and about 0.9, between about 0.25 and about 0.75, about 0.5, etc.). In some of these variations, all or only a subset of previously measured and stored dry item weights may be used when determining the lowest stored dry item weight. For example, the predetermined weight threshold may be equal to the lowest dry item weight out of the preceding 5, 10, 15, 20 (or other suitable number) measurements performed and stored, or a fraction of such lowest dry item weight. As another example, the predetermined weight threshold may be equal to the lowest dry item weight out of all measurements performed and stored in the preceding 10 minutes, 30 minutes, 1 hour, 2 hours (or other suitable time period), or a fraction of such lowest dry item weight.

Furthermore, the method may include responding differently to different predetermined weight thresholds in order to identify whether a weighing event has occurred. For example, if a measured weight is below a first, lower weight threshold value (e.g., about 2 grams), then no response action may be taken. If a measured weight is above a second, higher weight threshold (e.g., about 10 grams), then the measured weight may be considered a wet weight corresponding to a weighing event. If a measured weight is between the lower weight threshold value and the higher weight threshold value, then the method may include prompting the user to confirm whether a weighing event has occurred.

Additionally or alternatively, a weighing event may be determined based on detection of a stable measurement reading (e.g., substantially no fluctuation in measured weight, such as fluctuation only within a predetermined measurement range) for a predetermined threshold of time. For example, the predetermined measurement range may be about ±0.1 grams, ±0.07 grams, ±0.05 grams, ±0.02 grams, ±0.01 grams, etc., and the predetermined threshold of time may range between about 1 second and 5 seconds, between about 2 second and 4 seconds, etc. Combinations of various suitable conditions (e.g., detecting a threshold weight value for at least a predetermined period of time) may be used to identify a weighing event.

As yet another example, a weighing event may be determined based on user input, such as a user interacting with a user interface (e.g., buttons on the scale, user-manipulable or touch-sensitive icons on a displayed user interface, voice commands, etc.) to confirm the existence of a weighing event.

Furthermore, in some variations, the method may include applying a machine learning algorithm to distinguish between fluctuations in weight measurements due to weighing events (e.g., due to placement of at least one fluid-collecting item on the scale) and those due to non-weighing events, such as fluctuations caused by repositioning of a receptacle on the scale, fluctuations caused by shaking of a surface on which the scale rests, and/or fluctuations caused by vibrations when personnel walks near the scale or when machinery or equipment is operated near the scale, etc. For example, a training data set of scale measurement signals may be generated based on signals gathered during known weighing events and known non-weighing events, and a machine learning algorithm (e.g., data clustering algorithm, etc.) may be trained using the training data set and subsequently applied to identify when a scale signal pattern is associated with a weighing event or one or more types of non-weighing events. Additionally or alternatively, in some variations, a signal processing algorithm may be applied to time-based signals. For example, frequency domain transforms (e.g., Fourier transforms, etc.) may be applied to the scale signal after intervals of 0.5 seconds, 1 second, 2 seconds, or 5 seconds, etc., to determine the frequency of a signal variation. This interval may be shortened or lengthened based on one or more various factors or conditions, such as an identification of another weighing event as described above (e.g., the difference in stabilized weight crossing a particular threshold to recognize a weighing event). The determined frequency of signal variation may then be applied to a learned model (e.g., classification model) to recognize whether the frequency is best matched to one or more particular pre-learned non-weighing events such as a person walking by, other objects being placed on the same surface as the scale (but not in the scale), nearby machinery, etc. Additionally, low-pass/high pass filtering techniques may be used to smooth out the scale signal over a given period of time to aid in signal processing. These filters may, for example, be forward looking only, backward looking only, or some permutation of directionality in order to perform appropriate smoothing. Furthermore, recognition or identification of a weighing event or a non-weighing event may, in some variations, be determined using a suitable combination of frequency domain and signal smoothing/filtering techniques.

The method includes receiving a wet weight of the item 210, which may be in response to detecting the weighing event. For example, the scale may be pinged or prompted to communicate a weight measurement. As another example, the scale may substantially, continuously, or periodically communicate its weight measurement (e.g., every 0.05 seconds, 0.1 seconds, 0.5 seconds or every 1 second) and only a weight measurement following detection of the weighing event may be taken as a wet weight of the item and used for subsequent analysis as described elsewhere herein. In some variations, the wet weight of the item may be based on a single measurement value, or may be based on multiple measurement values (e.g., average) taken around the time of the weighing event. Upon receiving the wet weight of the item, the method may include storing the wet weight value in memory or another suitable data storage device.

The method may further include receiving a quantity of at least one item type 220 in the batch of weighed fluid-collecting items. The received quantity of item types may be used at least in part to determine total dry weight of all items being weighed in a particular batch. Although FIG. 2 shows that receiving a quantity of at least one item type 220 may be performed following receiving a wet weight of the at least one item 210, it should be understood that in other variations, receiving a quantity of at least one item type 220 may be performed prior to or substantially concurrently with receiving a wet weight of the least one item 210.

As shown in FIG. 3, in some variations, a user interface may prompt a user to enter quantity of each item or other substrate being weighed. Various item types may be displayed for selection by the user, such as surgical sponges (e.g., laparotomy sponges), surgical dressings, surgical gauze, surgical towels, absorbent pads or drapes (e.g., chux pads), vaginal packs and/or other textiles or absorbent items, etc. Additionally or alternatively, one or more types of containers holding any such textiles or other absorbent items (e.g., sponge count bag) may be displayed. Furthermore, the items may be biological (e.g., clot structure including fluid to be measured). Additionally, different sizes and/or brands of items (e.g., containers or other surgical item or substrate described herein) may be displayed for selection by the user. In some variations, the user interface may enable a user to enter a custom item type or other substrate not already presented as an option for selection, such as by providing a space for typing in an item type name and a dry weight associated with the item type and known by the user. Additionally or alternatively, the user may empirically determine and/or confirm a dry weight for an item or other substrate (e.g., custom item type) using the scale. For example, the user may weigh one or more dry samples of an item type of sufficient quantity so as to provide a statistical confidence as to the dry weight of a single sample of the item type. A dry weight of the item type may be estimated as the average dry weight for a single sample of the item type, based on the total weight and number of dry samples. Accordingly, the user interface may, for example, prompt the user to weigh at least a minimum number of dry samples of a new item type, prompt the user to input the quantity of dry samples of the new item type, measure the total weight of the dry samples, determine average dry weight of a single dry sample, prompt the user to input a custom item type name for the new item type, and store in memory (or any suitable data storage device) the average dry weight of a single dry sample as associated with the custom item type. The custom item type may be displayed for selection by the user during a medical procedure.

In one variation, as shown in FIG. 3, the item types may be presented in an array in combination with item counters. The item types may be identified, for example, with word labels and/or representative images or graphics (e.g., image of a type of unsaturated surgical textile may represent surgical textiles of that type). The item counters may be incremented and/or decremented by the user (e.g., by touching designated icons for incrementing and/or decrementing) to indicate the quantity of each type of item being weighed. Alternatively, the item types may be listed in drop-down menus or presented for selection in any suitable manner. Furthermore, in addition or alternative to displaying item counters to indicate quantity, the user interface may display a text box prompting the user to manually type in a quantity of item type, display a user-rotatable numbered dial, or facilitate user input of quantity of one or more item types in any suitable manner. Upon input of the quantity of item types, the user may confirm the selection (e.g., by selecting a displayed "analyze" icon as shown in FIG. 3, or any suitable icon).

The method may, in some variations, include storing and displaying a subset of selectable item types under certain circumstances. For example, the method may include storing selected types of items as "favorites" or "preferred item types", etc., such as selected types for particular kinds of medical procedures (e.g., chux for labor and delivery), selected brands for particular medical institutions (e.g., where a hospital may stock only a particular brand of an item type), etc. Furthermore, during a medical procedure with multiple batches of items for weighing, the method may include automatically suggesting items types during the procedure, such as based on item types previously selected during the same procedure or in previous procedures of the same procedure type. Storing and displaying a subset of selectable item types under certain circumstances may, for example, reduce time needed for the user to input quantities of one or more item types.

In yet other variations, the method may include using computer vision techniques to estimate or predict the quantity and/or item types being weighed. For example, the method may include generating or receiving an optical image of the items on the scale (e.g., on a bucket or tray on the scale), and a classification algorithm, etc. may be applied to the image data for determining a number and/or type of items on the scale. As another example, the method may include using an infrared (IR) depth-sending camera to perform a 3D scan of the items on the scale and determine contours of the items present on the scale. The method may include applying a classification algorithm to classify the batch of items on the scale as including a particular number of items and/or item type. The classification algorithm may, for example, base its classification on contour features of piles or collections of textiles known to include zero, one, two, etc. items of particular item types. The predicted quantity and/or item types being weighed may, in some variations, be confirmed by a user before being used in subsequent analysis.

Based on the quantity of the at least one item type being weighed, the method may include receiving a dry weight of the at least one item type 222. The dry weight for a single instance of each item type may, for example, be stored in memory or other suitable data storage device, as part of a look-up table, hash function, etc. such that the dry weight may be retrieved or received upon knowing the type or types of items that have been weighed. A total dry weight of multiple items may be determined by, for example, multiplying the dry weight of a single instance of an item type by the quantity of the item type to achieve a subtotal dry weight of each item type, then summing the subtotal dry weights of multiple item types to determine the total dry weight.

Additionally or alternatively, in some variations, the method may include weighing one or more items before being used to collect fluid. For example, weighing the one or more items may directly generate dry weight values of the items (e.g., instead of receiving the values from a stored memory, or to confirm the values received from a stored memory). Each individual item may be separately weighed, or groups of items of the same type may be weighed (whereupon collective weight may be divided by the number of items to estimate the dry weight of a single instance of that item type).

In some variations, weighing the one or more items and/or receiving a quantity of item types may be used to help track surgical items (e.g., textiles) used in a medical procedure. For example, surgical textiles may, during a medical procedure, be placed inside a patient to absorb blood and be subsequently removed (e.g., upon saturation or after the procedure is complete). However, there is a risk that at least some textiles may be inadvertently retained inside the patient, which may harm patient health such as by causing infection or even death. One approach to reduce the retention of foreign objects in a patient is to perform a count before and after (or throughout) the procedure, and make sure that the "before" and "after" counts are equal such that all objects are accounted for. For example, in one variation, weighing the one or more items may be used to help facilitate an accurate pre-procedural "before" count of items (e.g., textiles). Such a "before" count may be performed, for example, by receiving an item type to be counted (e.g., based on user input, machine vision techniques if the item is in the field of view of an image sensor, etc.), measuring a total weight of a batch of one or more dry or unused items of the item type, and dividing the total weight by a known dry weight of the item type. Furthermore, receiving a quantity of item types of items being weighed (e.g., after the fluid-collecting items are removed from the patient) may be help facilitate an accurate "after" count of used items throughout and/or after the procedure. Such "before" and "after" item counts may be compared to help reduce the risk of inadvertent foreign object retention in the patient, which may be harmful to the patient. A discrepancy in the "before" and "after" counts may prompt medical staff to locate any apparently missing textiles or other items, perform a recount, perform an X-ray scan of the patient, or perform other risk mitigation. Additionally or alternatively, a complementary "after" count of dry or unused items may be performed in a manner similar to that described for performing a "before" count, by receiving an item type, measuring total weight of dry or unused items that that are left over after the procedure, and dividing the total weight by a known dry weight of the item type. In one illustrative example of how to use the complementary "after" count of dry or unused items, a discrepancy between the "before" count compared to the sum of the "after" count of used items and the complementary "after" count of unused items may prompt medical staff to perform risk mitigation (e.g., searching for apparently missing items, recounting, performing an X-ray scan of the patient, etc.).

Furthermore, weighing the one or more items may help facilitate an accurate count of items to be used during the medical procedure in view of potential mispackaging or erroneous manual counting, etc. For example, an unused pack or collection of surgical textiles of the same type has an expected total dry weight given the number of textiles (e.g., ten) and a known dry weight of an individual textile of that type. However, if the pack of textiles is weighed and its total weight deviates significantly from the expected total dry weight, it may signify that the pack of textiles has been mispackaged or mislabeled, and may indicate that more or fewer textiles than expected are included in the pack. Accordingly, if the actual weight is sufficiently different from the expected weight (e.g., is greater than or less than at least half the known dry weight of an individual textile of that type), then the method may include alerting the user to review, recount, or otherwise reassess the number of textiles in the pack.

Upon receiving both the wet and dry weights of the item (or items) containing a first volume of a first fluid, the method may include estimating a first volume of the first fluid 230 based on a difference between the wet weight and the dry weight of the item. Furthermore, the method may, in some variations, include dividing the difference between the wet weight (mass) and the dry weight (mass) of the item or items by the density of the fluid, in accordance with Equation 1 below:

$$\text{volume of fluid in item} = \frac{\text{wet weight of item} - \text{dry weight of item}}{\text{density of fluid}} \quad (1)$$

For example, in one variation, the method may be used to estimate a volume of blood, which has a density of about 1.06 g/ml. Accordingly, to estimate a volume of blood in a weighed item, the method may include dividing the difference between the item's wet weight and dry weight (expressed in grams) by 1.06 g/ml, resulting in an estimate of the volume of blood expressed in milliliters.

In some variations in which the method is used to estimate a volume of a fluid which has a density of roughly 1.0 g/ml, the difference between the wet weight and the dry weight in grams may, in some applications, provide a sufficient estimate of volume of fluid in the weight items and the step of dividing the difference in wet and dry weights by the density of fluid may be omitted. For example, the step of dividing by the fluid density may be omitted if only a rough estimate of blood is required (since blood has a density generally approximating 1.0 g/ml), or a volume of urine or other fluid with a density of about 1.0 g/ml is being estimated in the weighed items.

In other variations, the difference between wet and dry weights in units of force (e.g., Newtons) may be used to estimate volume of fluid, such as by compensating for acceleration of gravity (e.g., 9.8 m/s2) in Equation 1.

Figure 4:
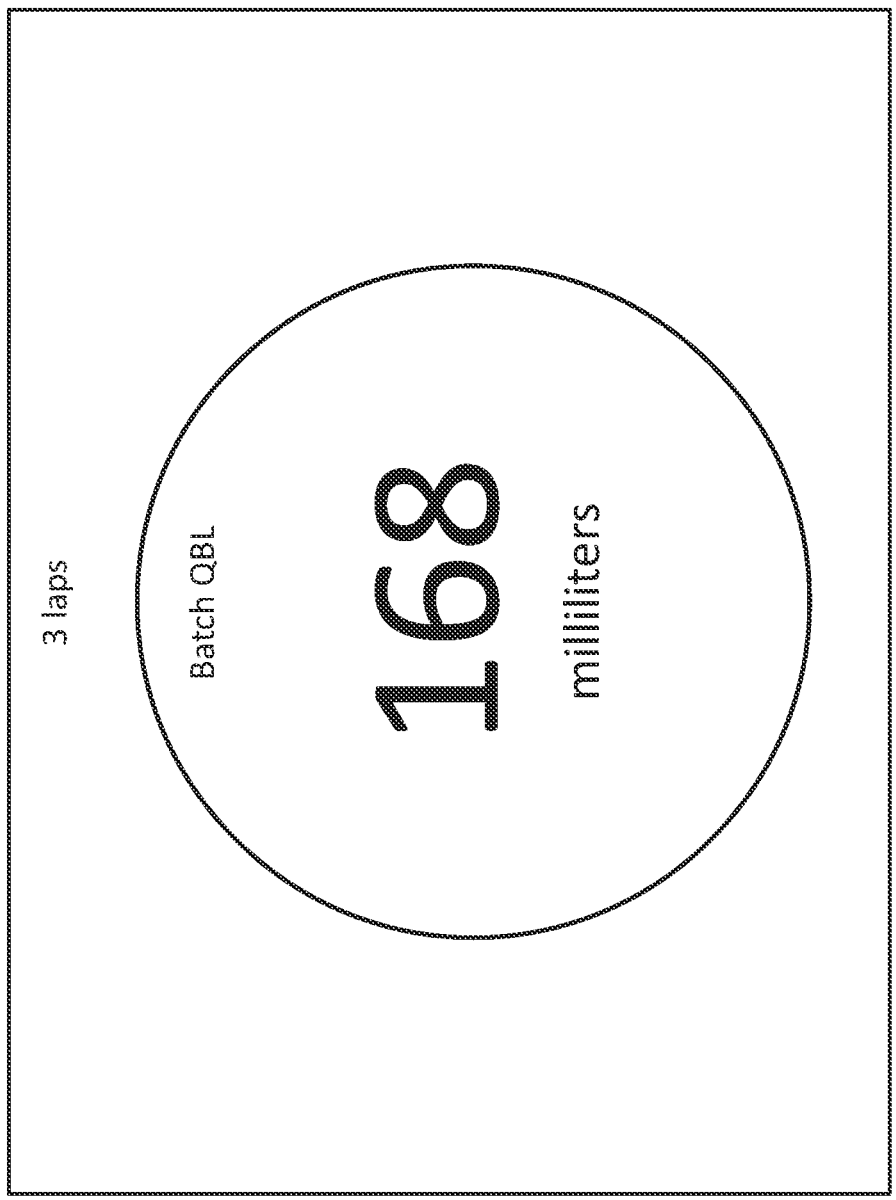
FIG. 4 is an exemplary user interface displaying an estimated quantity of a volume of fluid contained in a weighed item.

The method may include displaying the estimated volume of fluid to the user. For example, as shown in FIG. 4, the method may include displaying on a user interface a quantified blood loss (QBL) that has collected in a weighed batch of items containing blood. The method may further include displaying the quantity and item types of items that contain the volume of blood, which may, for example, help confirm to the user the correct number and item type were used to determine the dry weight value used in the analysis. The quantity and item type may, for example, be displayed as words as shown in FIG. 4, but additionally or alternatively may be displayed with representative graphics or images.

Although in some variations, the method may additionally or alternatively include weighing and analyzing items (e.g., textiles, etc.) that collect fluids by soaking or absorbing fluids, in some variations, the method may additionally or alternatively include weighing or analyzing items (e.g., V-shaped blood collection drape, canister) that collect fluids in a receptacle. For example, a volume of fluid collected in a container may be estimated in a process similar to that described above. A container may be associated with a first weight (e.g., an empty weight, dry weight, or other baseline reference weight such as weight of the container including an amount of fluid previously estimated), then weighed to determine a second weight (e.g., a wet weight or other measurement weight to be compared to the baseline reference weight). The difference between the first and second weights may be divided by the density of the fluid to estimate a volume of fluid in the container (or additional volume of fluid since the previous estimation). This estimate of fluid in the container may, for example, be used to confirm or corroborate other estimations of volume (e.g., those based on reference markers on the container).

Other Fluid-Collecting Items

As described above, some containers or other receptacles may be used to collect fluids lost by a patient. For example, a V-shaped blood collection drape (e.g., for labor and delivery applications of the method) or a canister may collect fluids without soaking or absorbing the fluid. When a fluid of interest (e.g., blood) is collected in one or more such containers, estimates of the fluid in the containers may be combined with estimates of the fluid in the weighed items (e.g., estimated as described above) to generate an aggregate total of volume of the fluid lost by the patient.

In some variations, a fluid of interest (e.g., blood) may be collected in a container in combination with one or more other secondary fluids of interest. Where the different fluids have different densities and are substantially immiscible, the different fluids may separate into different layers within the container, such that a total volume of fluid in the container may include at least a first layer portion including one fluid and a second layer portion including another fluid. For example, as shown in the illustrative schematic of FIG. 1, a container 130 may include total fluid volume 136 that includes a volume of a second fluid 132 and a volume of a fluid of interest 134. Furthermore, the container may include markings (e.g., graduated or calibrated markings) to facilitate estimation of fluid volumes. For example, in a labor and delivery procedure, both blood and amniotic fluid may be collected in a V-shaped blood collection drape placed underneath the patient. Accordingly, as shown in FIG. 2, in one variation, the method may include displaying a graphical representation of a container 240 containing a volume of a second fluid and a second volume of a first fluid of interest. The graphical representation of the container may include one or more display elements for receiving one or more user inputs indicating a volume of one or more of the fluids contained in the container.

Figure 5A:
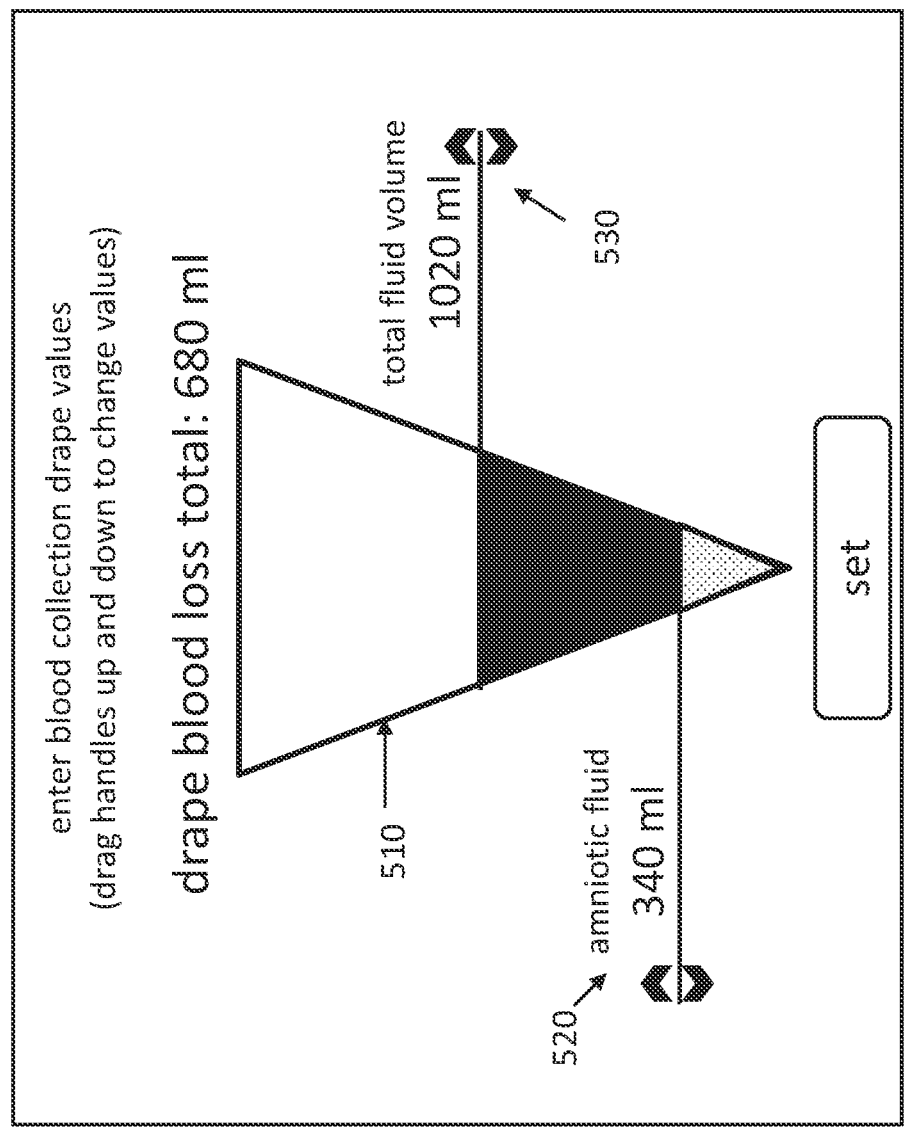
FIG. 5A is an exemplary user interface displaying a graphical representation of a container and display elements for user inputs.
Figure 5B:
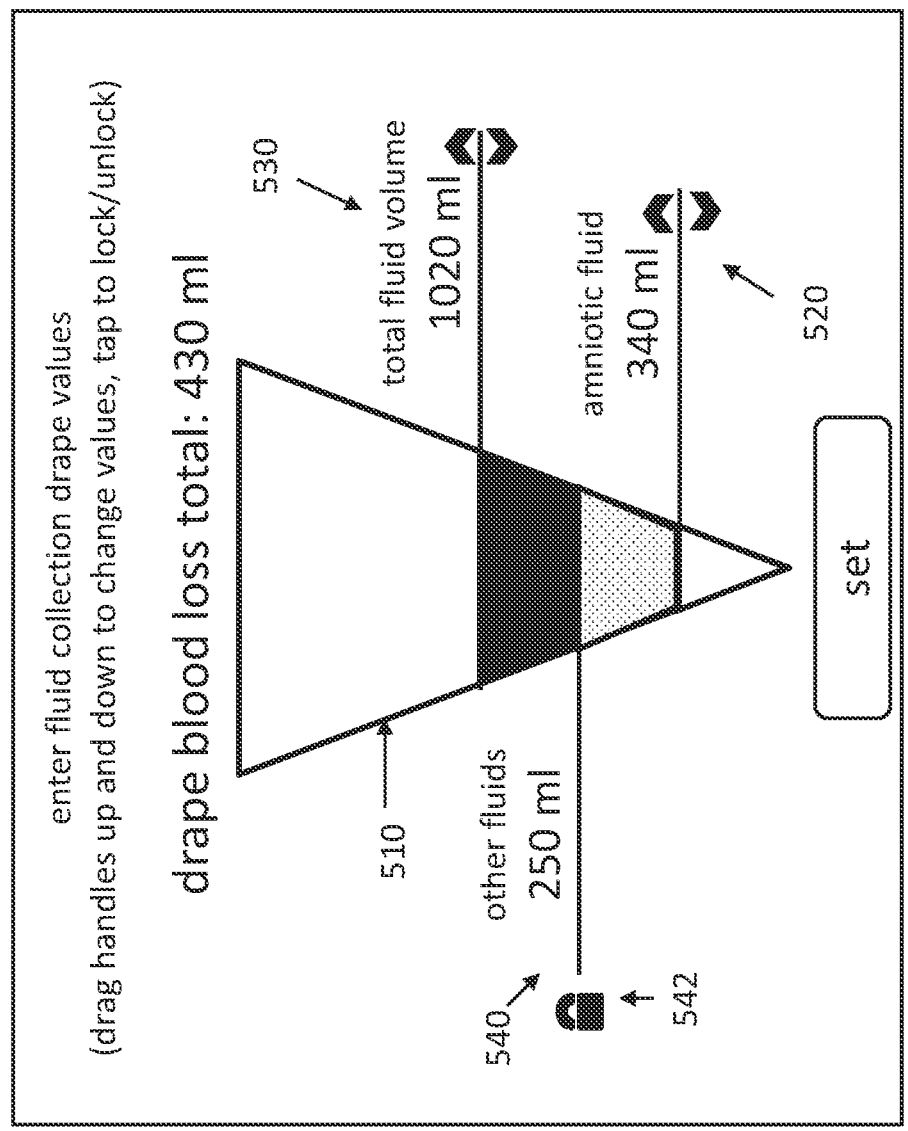
FIG. 5B is another exemplary user interface displaying a graphical representation of a container and display elements for user inputs.

FIG. 5A shows an exemplary graphical representation 510 of a V-shaped blood collection drape container. The graphical representation 510 may be generally triangular to mimic the structure of the V-shaped blood collection drape. The graphical representation may include a first display element 520 for receiving a first user input indicating the volume of the second fluid in the container and a second display element 530 for receiving a second user input indicating a total fluid volume (e.g., including the volume of the second fluid and the volume of the fluid of interest) in the container. The first and second display elements may directly correlate to fluid levels in the container itself (e.g., which may be estimated using fluid measurement markings on the container), such that the user need not perform mental calculations to estimate a separate volume of every individual type of fluid, thereby reducing inaccuracies in fluid loss estimations resulting from human error. Furthermore, the graphical representation may include additional display elements for receiving user inputs indicating additional volumes of fluid (e.g., a third display element for indicating volume of a third fluid, etc.). For example, as shown in FIG. 5B, the graphical representation 510 may include a third display element 540 for receiving a third user input indicating a volume of a third fluid.

The user input may involve manipulating the display elements relative to displayed fluid measurement markings corresponding to actual fluid measurement markings on the actual container, so as to mirror the relative positions of actual fluid levels and fluid measurement markings on the actual container. For example, the first display element 520 may be configured to indicate a volume of amniotic fluid (which may be estimated directly from markings on the container), and the second display element 530 may be configured to indicate a total volume of fluid including the amniotic fluid and blood (which may also be estimated directly from markings on the container). Furthermore, in variations in which a third display element 540 is included in the graphical representation of the container, the third display element 540 may be configured to indicate a known volume of another fluid such as a saline or antiseptic wash (e.g., that has been poured over the patient's birthing area to disinfect the area). Accordingly, in some variations, before manipulating the display elements, a user may not be required to mentally calculate the volume of blood based on a difference between relevant markings on the container, thereby reducing inaccuracies in blood loss estimation.

As shown in FIG. 5A, the first and/or second display elements 520 and 530 may include sliding markers that are user-manipulable and movable up and down along the depth of the graphical representation of the container. For example, when displayed on a touch-sensitive display, the user input may be received by a user touch on the display in which the user touches and drags the sliding markers to desired positions, taps the sliding markers (or increment counter elements, or selected portions of the graphical representation of the container, etc.) to selectively increment or decrement them to desired positions, etc. In response to detecting the positions of the first and second display elements 520 and 530, the method may include adjusting the estimated fluid volumes based on the detected positions of the first and second display elements 520 and 530 (e.g., adjusting an estimated volume of the second fluid based on the detected position of the first display element 520, adjusting an estimated total fluid volume based on the detected position of the second display element 530, etc.). The numerical volume values may be displayed adjacent the sliding markers.

Figure 7:
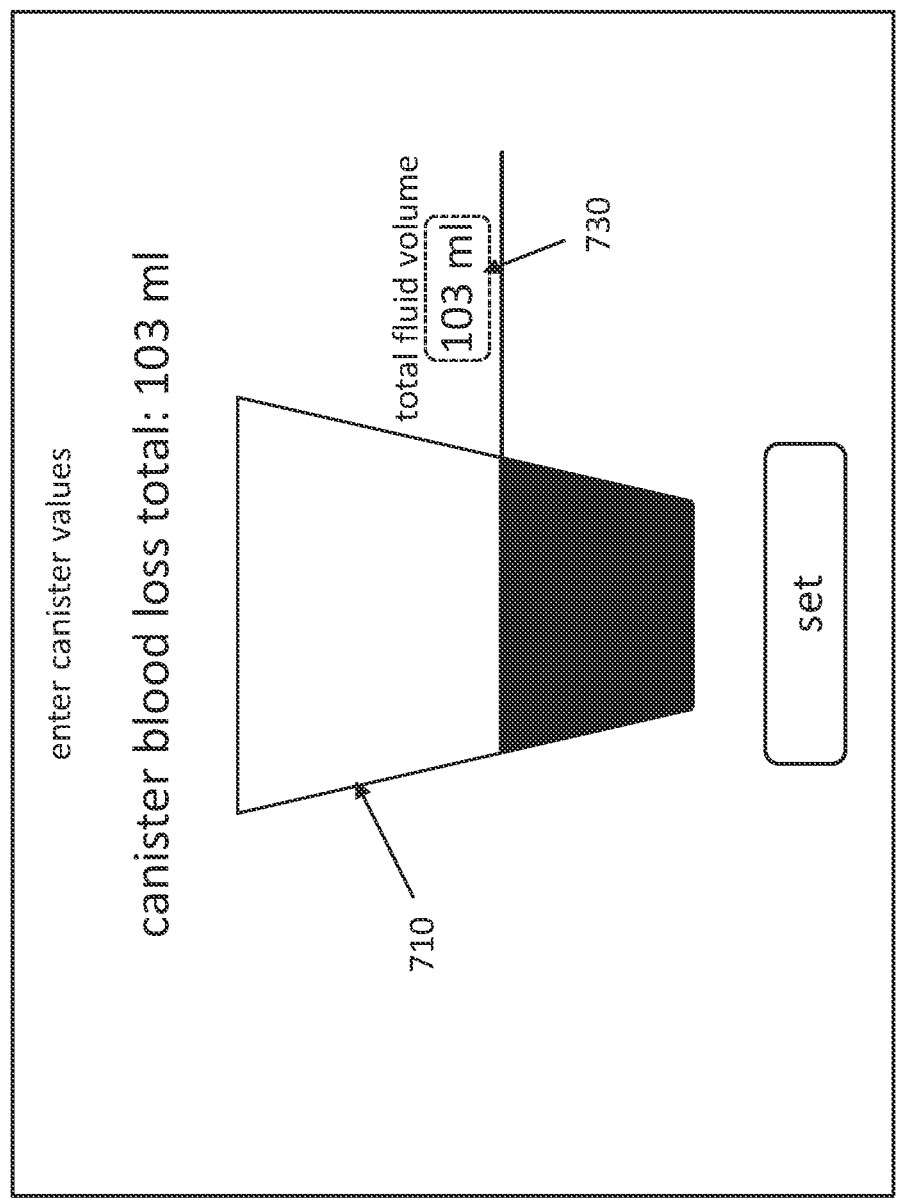
FIG. 7 is another exemplary variation of a user interface displaying a graphical representation of a container and display elements for user inputs.

In other variations, the first and/or second display elements 520 and 530 may additionally or alternatively have any other suitable form for receiving user input indicating fluid volumes. For example, in one variation as shown in FIG. 7, a display element may include a text box 730 into which the user may type or otherwise enter a fluid volume value.

As shown with reference to display element 540 in FIG. 5B, in some variations, at least one of the display elements may be locked or otherwise fixed at a particular value. For example, at least one of the display elements may be locked at a volume value such that an affirmative action may be required to further adjust the volume value indicated by the display element. Any suitable user input may initiate locking and/or unlocking of the display element, such as a user's tap on the display element after the display element is adjusted to the desired position, double-tapping, selection of a separate lock button or other icon, vocal command, etc. Additionally or alternatively, a custom on-screen touch gesture (e.g., tracing of a circle, dual or triple finger swipe or slide gesture, etc.) may be suitable user input for initiating locking and/or unlocking of the display element. A display element that is locked may be indicated with a displayed "lock" icon 542, or any suitable indication (e.g., the word "lock", a change in color of the display element, a change in text font in the display element, etc.).

In other variations, only one display elements may be displayed for receiving user input indicating a volume of fluid contained in the container. For example, the method may include displaying a graphical representation of a container containing only a volume of the fluid of interest (e.g., blood). FIG. 7 shows an exemplary graphical representation 710 of a suction canister containing substantially only one fluid (e.g., blood that has been collected by a suction wand). The graphical representation 710 may be, for example, frustoconical or generally rectangular. The graphical representation 710 may include a display element 730 for receiving a user input indicating the volume of the fluid in the container. Similar to the display elements 520 and 530 described above, in some variations, the display element 730 may include a sliding marker that directly corresponds to a fluid level in the container itself that may be estimated using fluid measurement markings on the container. Alternatively, as shown in FIG. 7, the display element may include a textbox into which a user may enter a fluid volume value.

Figure 8:
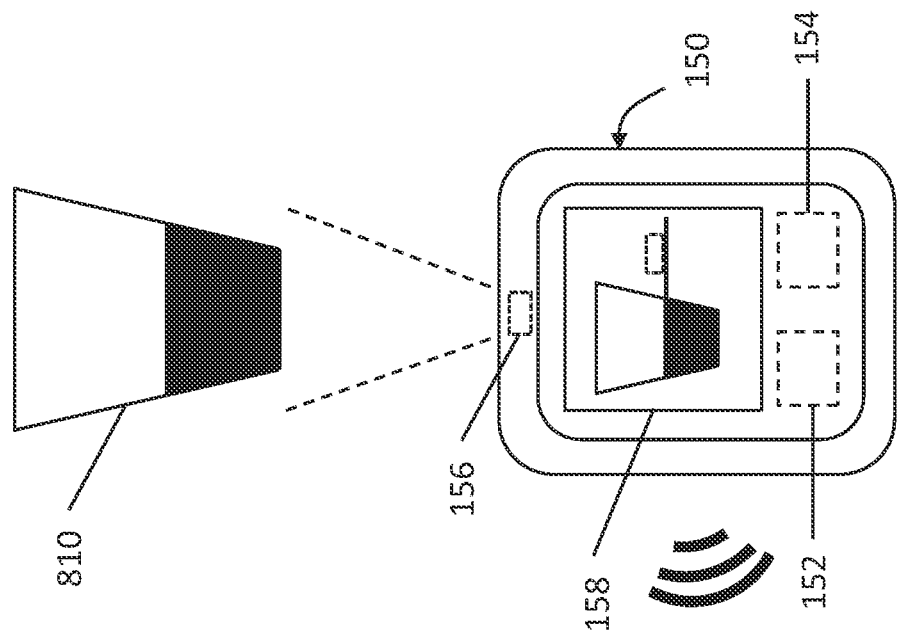
FIG. 8 is an illustrative schematic of another variation of a system for quantifying fluid from a patient.
Figure 8:
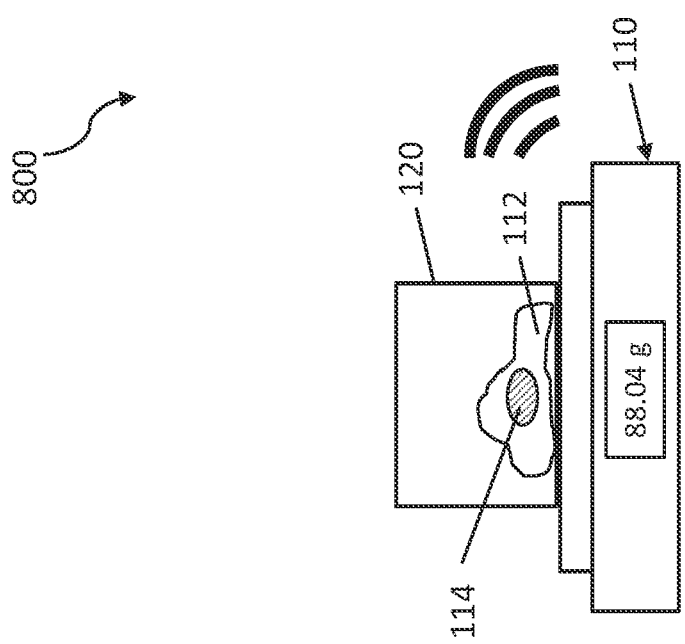

In yet other variations, one or more fluid volumes in the container may be estimated based on an optical image of the container. For example, as shown in FIG. 8, one or more optical images may be taken with a camera or other suitable optical sensor whose field of view includes the container containing a volume of a fluid of interest. As such, the method may include capturing a static, single-frame image including at least a portion of the fluid container, and/or a multi-frame video feed including multiple static images of the fluid container. For example, static images may be taken periodically (e.g., every ten seconds, every thirty seconds, etc.) or upon a user-input or other trigger event. The image can be a color image, a black and white image, a grayscale image, an infrared image, a field of view of an optical sensor, a fingerprint of a field of view of an optical sensor, a point cloud, or any other suitable type of image.

One or more machine vision techniques may be used to estimate fluid volumes in the container based on an optical image of the container. For example, generally, estimating fluid volume in the container may include using machine vision techniques in identifying a container-depicting region of an image of the container, correlating a portion of the container-depicting region with an estimated fluid level within the container, and estimating a volume of fluid within the container based on the estimated fluid level. Suitable vision techniques include segmentation techniques (e.g., edge detection, background subtraction, grab-cut algorithms, etc.), gauging, clustering, pattern recognition, template matching, feature extraction, descriptor extraction (e.g., extraction of texton maps, color histograms, HOG, SIFT, MSER (maximally stable external regions for removing blob-features from the selected area), etc.), feature dimensionality reduction (e.g. PCA, K-Means linear discriminant analysis, etc.), feature selection, thresholding, positioning, color analysis, parametric regression, non-parametric regression, unsupervised or semi-supervised parametric or non-parametric regression, and/or any other type of machine learning or machine vision to estimate a physical dimension of the container and/or its fluid contents.

Furthermore, estimating fluid volume in the container may include implementing suitable machine vision techniques to identify fluid level markings printed (and/or embossed, adhered, etc.) on the fluid container and identifying the fluid boundaries (e.g., boundary between layers of different fluids, surface of total fluid volume, etc.) within the canister. Fluid boundaries may be identified, for example, based on transitions in color of pixels along the height (e.g., vertical line of pixels) along the container-depicting image region. For example, upper and lower boundaries of blood in a container may be identified based on abrupt shifts between red and non-red colors along a vertical line of pixels in the container-depicting image region. The method may further estimate the volume of one or more fluids within the canister based on one or more identified fluid boundaries relative to one or more identified fluid level markings on the container.

Another variation of estimating fluid volume in the container using images includes using machine vision techniques to identify a float or other reference point corresponding to a fluid level in the container. The identified position of the float can be used, such as by comparing the float to optical fiducials, to estimate fluid volume.

In another variation, fluid volume in the container may be automatically estimated based on one or more fluid level sensors. For example, fluid level may be detected with one or more point-level sensors that indicate whether the fluid volume in the container is above or below a particular threshold sensing point. As another example, fluid level may be detected with one or more continuous-level sensors that measure the fluid level in the container and indicates a numerical value corresponding to fluid volume. Any suitable fluid level sensor may be used to detect fluid volume in the container and generate a fluid level signal that indicates the detected fluid volume. For example, capacitance level sensors, conductive level sensors, ultrasonic level sensor, and/or optical sensors, etc. may be appropriate as point-level and/or continuous-level sensors.

Other examples of estimating fluid volume in a container are described in U.S. Pat. No. 9,171,368, entitled "System and method for estimating a quantity of a blood component in a fluid canister," as well as U.S. patent application Ser. No. 15/154,917, entitled "Systems and methods for assessing fluids from a patient," each of which is hereby incorporated in its entirety by this reference. In other variations, the method may include any suitable process for estimating fluid volume in the container.

Aggregation of Fluid Estimations

Following estimation of the first and second volumes of a first fluid (e.g., fluid of interest such as blood) among weighed fluid-collecting items and other fluid-collecting items, the method may include estimating a quantity of the first fluid 280 based at least in part on the estimated first and second volumes of the first fluid. For example, the estimated quantity of the first fluid may be an amount of loss (e.g., volume) based on a sum of the estimated first and second volumes of the first fluid (e.g., fluid collected in the weighed items and other non-weighed items). As another example, the estimated quantity of the first fluid may be a volumetric rate of loss based on a sum of the estimated first and second volumes of the first fluid (and any other volumetric estimates of fluid analyzed previously for the same patient) and the duration of time over which the first fluid has been lost by the patient. Additionally or alternatively, the method may include generating a present fluid loss trend in the amount or rate of loss over time (e.g., over the course of the medical procedure), and/or generating a predicted future fluid loss trend based on the present fluid loss trend.

Figure 6:
FIG. 6 is an exemplary user interface displaying estimated quantities of a fluid.
Figure 9:
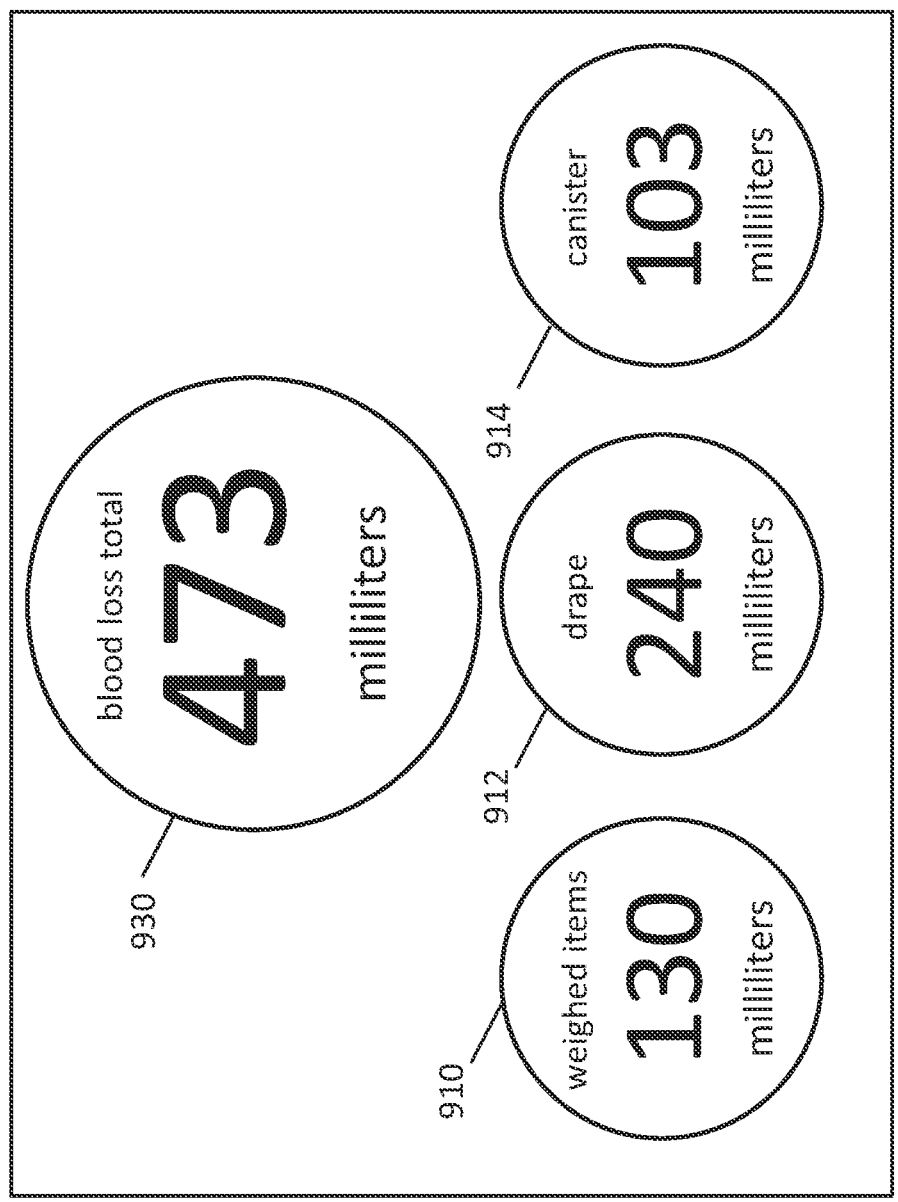
FIG. 9 is another exemplary variation of a user interface displaying estimated quantities of a fluid.

The method may further include displaying the estimated quantity of the first fluid, and/or the breakdown of individual volumes of fluid across the different categories of fluid-collecting items. For example, as shown in FIG. 6, an estimated first volume of fluid in weighed items may be displayed as a first subtotal 610, and an estimated second volume of fluid from a container (e.g., V-shaped blood collection drape) may be displayed as a second subtotal 612. Furthermore, an estimated total quantity of the fluid may be displayed as a fluid loss total 630. As another example, as shown in FIG. 9, in addition to a first subtotal 910 and a second subtotal 912 similar that shown in FIG. 6, another estimated volume of fluid from a weighed container or container whose contents were entered by a user or detected automatically through machine vision techniques and/or sensors (e.g., a blood collection drape or suction canister) may be displayed as a third subtotal 914. More or fewer subtotal volumes of fluid may be displayed, which may depend, for example, on the number of individual categories of fluid-collecting items that are considered. Furthermore, in other variations, different kinds of subtotals may be displayed (e.g., estimates of fluid collected by different kinds of weighed items). Additionally or alternatively, the method may include displaying the generated present fluid loss trend and/or predicted future fluid loss trend.

In some variations, the method may include comparing the estimated quantity of the first fluid (or other fluid of interest) with a predetermined threshold for lost fluid, and triggering an alarm if the volume of first fluid meets the predetermined threshold. The alarm may be visual (e.g., displayed on a display) or audible over speakers, etc. In one variation, the estimated amount of loss of the first fluid may be compared to a threshold. For example, in a labor and delivery application of the method, if an estimated total amount of blood lost by the patient (and which is collected by items subsequently weighed and/or in other items) exceeds about 500 milliliters, then an alarm may be triggered to warn medical personnel of the possibility of patient hemorrhage that may endanger the health and life of the patient. In another variation, the estimated volumetric rate of loss of the first fluid may be compared to a threshold.

In another variation, the generated present fluid loss trend and/or predicted future fluid loss trend may be compared to one or more representative reference data sets. A representative reference data set may be identified from a stored database of data based on, for example, one or more health condition or disease factors, practice-based factors, patient type (e.g., sex, age, weight, ethnicity, etc.), and/or other suitable patient- or procedure-related factors. For example, a set of reference fluid loss values may include an average, median, mode, or a range of historical fluid loss values from a plurality of prior procedures, each of which may or may not be the same type as the current procedure. Based on a similarity determined between the patient's data and the representative reference data, the method may include triggering an alarm indicating predicted danger to the patient (e.g., predicted excessive future blood loss). Other examples of generating and utilizing fluid loss trends are described in U.S. patent application Ser. No. 15/154,921, entitled "Method for projecting blood loss of a patient during a surgery," which is hereby incorporated in its entirety by this reference.

Systems for Quantifying Fluids

As shown in FIG. 1, a system 100 for quantifying fluid from a patient may include a scale 110 configured to measure a wet weight of at least one item containing a first volume of a first fluid, a display 158 configured to display a graphical representation of a container containing a least a second volume of the first fluid, and a processor 154 coupled to the scale 110 and the display 158. For example, the graphical representation may represent a container 130 including a total fluid volume 136 that includes a volume of a second fluid 132 and a volume of the first fluid 134. Furthermore, as described above, in some variations, the graphical representation may include a first display element for receiving a first user input indicating the volume of the second fluid in the container, and a second display element for receiving a second user input indicating a total fluid volume in the container. Generally, the system 100 may, in some variations, be configured to substantially perform any of the variations of the method 200 described in further detail above.

Some or all of the system may be in an integrated device and placed near the patient during the medical procedure (e.g., in the operating room or delivery room) to assess patient fluids that are lost and collected by weighable items and/or containers. For example, the system may at least partially include a handheld or mobile computing device 150 (e.g., that executes a native fluid analysis application program). Such a handheld or mobile device may, for example, be a tablet computer, laptop computer, mobile smartphone, etc. which may include a camera, processor, and display. However, in other variations, some or all of the system components may be separated as discrete, interconnected devices. For example, the camera and/or display may be located substantially near the patient during the procedure, while the processor may be located at a remote location (e.g., in the operating room or delivery room separate from camera and/or display, or outside the operating room or delivery room), communicating with the camera and display through a wired or wireless connection or other network.

The scale 110 may be an electronic or digital scale having suitable range and resolution for measuring medical or surgical items containing fluid. For example, the scale may be configured to measure loads up to a maximum load ranging between about 100 grams and 10,000 grams, between about 250 grams and 750 grams, at least about 500 grams, etc. The scale may further be configured to measure loads with a precision of at least 0.01 grams, at least 0.1 grams, at least 1 gram, etc. In some variations, the scale 110 may be wireless (e.g., communicating with Bluetooth or other suitable communication protocol) and configured to communicate with the processor 154 remotely. Additionally or alternatively, the scale 110 may be configured to communicate with the processor 154 via a wired connection. Wireless or wired communication status may be indicated to the user. For example, confirmation of functional communication between the scale 110 and the processor 154 may be displayed (e.g., on a display as shown in FIG. 3), and/or audibly indicated to the user. As another example, any interruption in communication between the scale 110 and the processor 154 may be detected and indicated to the user on a display or audibly, etc. as an alert or warning.

As shown in FIG. 1, the scale 110 may be equipped with a receptacle 120 (e.g., bin, bucket, tray) configured to receive the one or more items to be weighed. The receptacle 120 may include a raised rim or lip to help contain any fluids that may seep or escape from the items being weighed.

Generally, one or more processors 154 may be configured to execute the instructions that are stored in memory 152 such that, when it executes the instructions, the processor 152 performs aspects of the methods described herein. The instructions may be executed by computer-executable components integrated with the application, applet, host, server, network, website, communication service, communication interface, hardware/firmware/software elements of a user computer or mobile device, wristband, smartphone, or any combination thereof. The instructions may be stored on memory or other computer-readable medium such as RAMs, ROMs, flash memory, EEPROMs, optical devices (e.g., CD or DVD), hard drives, floppy drives, or any suitable device.

Generally, in one variation, the processor 154 may be configured to estimate the first volume of the first fluid in the weighed item based on a difference between a dry weight of the item and the wet weight of the item, estimate the second volume of the first fluid in the container based at least in part on the first and second user inputs, and estimate a total quantity of the first fluid based at least in part on the estimated first and second volumes of the first fluid. The processor 154 may additionally or alternatively be configured to perform some or all aspects of any of the variations of the methods described herein. As described above, the one or more processors 154 may be integrated into a handheld or mobile device 150. In other variations, the one or more processors 154 may be incorporated into a computing device or system, such as a cloud-based computer system, a mainframe computer system, a grid-computer system, or other suitable computer system.

The display 158 may be configured to display one or more of the estimated volumes of the first fluid and/or estimated total quantity (or predicted or future trends of loss, etc.) of the first fluid. The display 158 may be configured to display or otherwise communicate to a user (e.g., doctor, nurse) other information, including but not limited to patient information, images of containers or substrates, etc. The display 158 may include a screen on a handheld or mobile device, a computer monitor, a television screen, a projector screen, or other suitable display. In some variations, the display 158 may be configured to display a user interface that enables the user to input information (e.g., estimated volumes of fluid in one or more containers), select display options (e.g., font, color, language, etc.) and/or content (e.g., patient information, fluid-related information, alerts, etc.). In these variations, the display may be user-interactive and include a resistive or capacitive touch screen that is responsive to skin, a stylet, or other user contact. In other variations, the display 158 may be user-interactive via a cursor controlled by a mouse, keyboard, or other suitable input device.

In some variations, the system may additionally or alternatively include an audio system that communicated information (e.g., fluid-related information, alerts, etc.) to a user. The display and/or the audio system may, for example, provide alerts or alarms upon the estimated quantity of trend of fluid loss meeting a threshold, which may be useful to prompt certain actions in response, such as providing a blood transfusion to the patient.

Furthermore, in some variations, as shown in FIG. 8, a system 800 for quantifying fluid from a patient may be substantially similar to the system 100 shown in FIG. 1, except that the system may additionally or alternatively include a camera 156 or other optical sensor or optical imaging device configured to generate an image of a container 810 including a third volume of the fluid of interest. The camera 156 may include at least one optical image sensor (e.g., CCD, CMOS, etc.) that captures a color optical digital image with red, green, and blue (RGB) color components for the pixels, and/or other suitable optical components. For example, the camera 156 may include a single image sensor paired with suitable corresponding optics and/or filters (e.g., color filter arrays such as a Bayer pattern filter). As another example, the camera 156 may include multiple image sensors paired with suitable corresponding optics, such as at least one prism or diffractive surface to divide white light into separate color channels (e.g., RGB), each of which is detected by a respective image sensor. However, the camera 156 may include any suitable image sensor sand other optical components to enable the camera 156 to generate images.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed, as many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A computer-implemented method for quantifying a first fluid from a patient, the method comprising:
    displaying on a display a graphical representation of a container;
    receiving a first user input to a first display element on the display indicating a volume of a second fluid observed in the container;
    receiving a second user input to a second display element on the display indicating a total fluid volume observed in the container;
    estimating a first volume of the first fluid based on the first user input and the second user input;
    receiving a third user input to a third display element on the display indicating a quantity of each different type of absorbent articles, wherein the third display element is automatically selected for display from a group of display elements each associated with the different types of the absorbent articles, and wherein the third display element is selected based on at least one of a procedure type, a previous procedure type, a selected brand, and a user preference;
    estimating a total dry weight associated with the absorbent articles based on the third user input and a predetermined dry weight stored in memory and associated with each type of the absorbent articles;
    estimating a second volume of the first fluid contained in the absorbent articles based on a difference between the total dry weight and a wet weight of the absorbent articles;
    displaying on the display a graphical representation of the first volume of the first fluid as a fluid level within the graphical representation of the container;
    displaying on the display a graphical representation of the total fluid volume within the graphical representation of the container;
    displaying on the display a graphical representation of the volume of the second fluid within the graphical representation of the container;
    displaying on the display a graphical representation of the second volume of the first fluid; and
    wherein the graphical representation of the volume of the total fluid volume includes the graphical representation of the first volume of the first fluid and the graphical representation of the volume of the second fluid.

2. The method of claim 1, wherein the graphical representation of the container is a triangle to correspond to the container being a V-shaped blood collection drape, wherein the step of displaying on the display the graphical representation of the first volume of the first fluid further comprises incrementing or decrementing the displayed fluid level within the triangle to correspond to actual fluid levels of the first and second fluids within the V-shaped blood collection drape.

3. The method of claim 1, wherein the first and second display elements are sliding markers, wherein the step of receiving the first and second user inputs comprises receiving on the display a touch input incrementing or decrementing the sliding markers to desired set positions.

4. The method of claim 3, further comprising displaying on the display numerical volume values adjacent the sliding markers.

5. The method of claim 1, wherein the first display element corresponds to a volume of amniotic fluid, and wherein the second display element corresponds to the total volume of fluid including amniotic fluid and blood.

6. The method of claim 1, further comprising alerting a user if the estimated quantity of the first fluid meets a predetermined threshold.

7. The method of claim 1, further comprising:
    identifying a weighing event corresponding to one or more of the absorbent articles being placed on a scale by detecting a weight meeting a predetermined threshold value for at least a predetermined period of time; and
    receiving the wet weight in response to the identified weighing event.

8. The method of claim 1, wherein the first user input indicating the volume of the second fluid is based on an input of a fluid level of first fluid as observed in the container, and wherein the second user input indicating the total fluid volume observed is based on a fluid level of total fluid as observed in the container.

9. A computer-implemented method for quantifying amniotic fluid and blood from a patient, the method comprising:
  displaying on a display:
    a graphical representation of a container,
    a first display element,
    a second display element, and
    a third display element automatically selected from a group of display elements based on at least one of a procedure type, a previous procedure type, a selected brand of absorbent articles, and a user preference;
  receiving a first user input to the first display element on the display, wherein the first display element is configured to be incremented or decremented to a desired set position based on a fluid level of the amniotic fluid as observed in the container;
  receiving a second user input to a second display element on the display, wherein the second display element is configured to be incremented or decremented to a desired set position based on a fluid level of total fluid as observed in the container;
  receiving a third user input to the third display element on the display indicating a quantity of each different type of absorbent articles;
  displaying on the display graphical representations of the amniotic fluid and the total fluid within the graphical representation of the container;
  estimating a volume of amniotic fluid contained within the container based on the first user input;
  estimating a first volume of blood contained within the container based on the first user input and the second user input;
  receiving a predetermined dry weight associated with each of the different types of the absorbent articles from a memory device;
  estimating a total dry weight associated with the absorbent articles based on the third user input and the predetermined dry weight;
  estimating a second volume of blood contained in the absorbent article based on a difference between the total dry weight of the absorbent articles and a wet weight of the absorbent articles;
  estimating a quantity of blood based on the estimated first and second volumes of the blood; and
  displaying on the display the quantity of the blood.

10. The method of claim 9, wherein the first and second display elements are sliding markers, wherein the step of receiving the first and second user inputs comprises receiving on the display a touch input incrementing or decrementing the sliding markers to the respective desired set positions.

11. The method of claim 10, further comprising displaying on the display numerical volume values adjacent the sliding markers.

12. A system for quantifying fluid from a patient, the system comprising:
  a display configured to display:
    a graphical representation of a container,
    a first display element for receiving a first user input indicating a volume of amniotic fluid observed in the container,
    a second display element for receiving a second user input indicating a total fluid volume observed in the container, and
    a third display element automatically selected from a group of display elements based on at least one of a procedure type, a previous procedure type, a selected brand, and a user preference, wherein a third user input to the third display element is for indicating a quantity of each different type of absorbent articles;
  a scale configured to measure a total wet weight of the absorbent articles; and
  a processor coupled to the scale and the display, wherein the processor is configured to:
    estimate a first volume of blood in the container based on the first and second user inputs;
    receive a predetermined dry weight associated with each type of the absorbent articles from a memory device;
    estimate a total dry weight associated with the absorbent articles based on the third user input and the predetermined dry weight;
    receive the total wet weight of the absorbent articles from the scale;
    estimate a second volume of blood in the absorbent articles based on a difference between the total dry weight and the total wet weight of the absorbent articles; and
    estimate a quantity of blood based on the estimated first and second volumes of the first fluid,
  wherein the display is configured to display graphical representations of the volume of amniotic fluid and the total fluid volume within the graphical representation of the container; and
  wherein the first and second display elements are sliding markers, the display is a touchscreen display configured to receive a touch input incrementing or decrementing the sliding markers to desired set positions, and the processor is configured to increment or decrement displayed fluid levels within the container to correspond to actual fluid levels within the container based on the first and second user inputs.

13. The system of claim 12, wherein the display is further configured to display a graphical representation of the total fluid volume that is displayed within the graphical representation of the container.

14. The system of claim 12, wherein the display is further configured to display a graphical representation of the volume of the amniotic fluid that is displayed within the graphical representation of the container.

15. The system of claim 12, wherein the graphical representation of the container is a triangle to correspond to the container being a V-shaped blood collection drape, and the processor is further configured to increment or decrement displayed fluid levels within the triangle to correspond to actual fluid levels within the V-shaped blood collection drape.

16. The system of claim 12, wherein the first user input indicating the volume of the amniotic fluid is based on an input of a fluid level of amniotic fluid as observed in the container, and wherein the second user input indicating the total fluid volume observed is based on a fluid level of total fluid as observed in the container.

* * * * *